United States Patent
Holsten et al.

(10) Patent No.: US 10,154,833 B2
(45) Date of Patent: Dec. 18, 2018

(54) SPECIMEN RETRIEVAL DEVICE WITH POUCH STOP

(71) Applicant: Covidien LP, Mansfield, MA (US)

(72) Inventors: Henry Holsten, Hamden, CT (US); Thomas Zammataro, Hamden, CT (US); Jaroslaw T. Malkowski, Trumbull, CT (US); Peter Hathaway, Lebanon, CT (US)

(73) Assignee: Covidien LP, Mansfield, MA (US)

( * ) Notice: Subject to any disclaimer, the term of this patent is extended or adjusted under 35 U.S.C. 154(b) by 558 days.

(21) Appl. No.: 14/443,079

(22) PCT Filed: Feb. 27, 2014

(86) PCT No.: PCT/US2014/018959
§ 371 (c)(1),
(2) Date: May 15, 2015

(87) PCT Pub. No.: WO2014/134285
PCT Pub. Date: Sep. 4, 2014

(65) Prior Publication Data
US 2015/0289864 A1    Oct. 15, 2015

Related U.S. Application Data

(60) Provisional application No. 61/771,156, filed on Mar. 1, 2013, provisional application No. 61/771,152, filed
(Continued)

(51) Int. Cl.
*A61B 17/00* (2006.01)
*A61B 17/221* (2006.01)
*A61B 10/04* (2006.01)

(52) U.S. Cl.
CPC ........ *A61B 17/00234* (2013.01); *A61B 10/04* (2013.01); *A61B 17/221* (2013.01);
(Continued)

(58) Field of Classification Search
CPC ............ A61B 17/221; A61B 17/32056; A61B 17/22031; A61B 2017/00287–2017/0034;
(Continued)

(56) References Cited

U.S. PATENT DOCUMENTS 30,471 A    10/1860  Dudley
35,164 A     5/1862  Logan et al.
(Continued)

FOREIGN PATENT DOCUMENTS

DE    3542667 A1    6/1986
DE    8435489 U1    8/1986
(Continued)

OTHER PUBLICATIONS

International Search Report for PCT/US14/18959 date of completion is May 30, 2014 (2 pages).
(Continued)

*Primary Examiner* — Christopher L Templeton

(57) ABSTRACT

A specimen retrieval device includes an outer shaft defining a bore, an inner shaft slidably disposed within the bore of the outer shaft, a pouch detachably coupled to a distal end of the inner shaft, and a pouch retention mechanism configured to selectively retain the pouch at the distal end of the inner shaft.

15 Claims, 29 Drawing Sheets

Related U.S. Application Data on Mar. 1, 2013, provisional application No. 61/771,148, filed on Mar. 1, 2013, provisional application No. 61/771,144, filed on Mar. 1, 2013, provisional application No. 61/771,139, filed on Mar. 1, 2013, provisional application No. 61/771,138, filed on Mar. 1, 2013, provisional application No. 61/771,135, filed on Mar. 1, 2013, provisional application No. 61/771,132, filed on Mar. 1, 2013, provisional application No. 61/771,130, filed on Mar. 1, 2013, provisional application No. 61/771,129, filed on Mar. 1, 2013, provisional application No. 61/771,122, filed on Mar. 1, 2013, provisional application No. 61/771,120, filed on Mar. 1, 2013.

(52) U.S. Cl.
CPC .............. *A61B 2017/00287* (2013.01); *A61B 2017/00292* (2013.01); *A61B 2017/00336* (2013.01)

(58) Field of Classification Search
CPC .... A61B 2017/2212; A61B 2017/2215; A61B 2017/1205; A61B 2017/12054
See application file for complete search history.

(56) References Cited

U.S. PATENT DOCUMENTS

| | | |
|---|---|---|
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |

(56) References Cited

U.S. PATENT DOCUMENTS

| | | | |
|---|---|---|---|
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinski et al. |
| 8,206,401 B2 | 6/2012 | Nakao |
| 8,337,510 B2 | 12/2012 | Rieber et al. |
| 8,343,031 B2 | 1/2013 | Gertner |
| 8,348,827 B2 | 1/2013 | Zwolinski |
| 8,388,630 B2 | 3/2013 | Teague et al. |
| 8,409,112 B2 | 4/2013 | Wynne et al. |
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2008/0300616 A1* | 12/2008 | Que ................. A61B 17/12022 606/191 |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2011/0087235 A1 | 4/2011 | Taylor et al. |
| 2011/0184311 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1 | 8/2011 | Fleming et al. |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0083797 A1 | 4/2012 | Cabrera et al. |
| 2012/0203241 A1 | 8/2012 | Williamson, IV |
| 2013/0023895 A1 | 1/2013 | Saleh |
| 2013/0103042 A1 | 4/2013 | Davis |
| 2013/0116592 A1 | 5/2013 | Whitfield |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |

FOREIGN PATENT DOCUMENTS

| | | |
|---|---|---|
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| FR | 1272412 A | 9/1961 |

(56) References Cited

FOREIGN PATENT DOCUMENTS

| | | | |
|---|---|---|---|
| GB | 246009 | A | 1/1926 |
| WO | 93/15671 | A1 | 8/1993 |
| WO | 9315675 | A1 | 8/1993 |
| WO | 9509666 | A1 | 4/1995 |
| WO | 01/35831 | A1 | 5/2001 |
| WO | 2004002334 | A1 | 1/2004 |
| WO | 2004/112571 | A2 | 12/2004 |
| WO | 2005/112783 | A1 | 12/2005 |
| WO | 2006/110733 | | 10/2006 |
| WO | 2007/048078 | A1 | 4/2007 |
| WO | 2007/048085 | A2 | 4/2007 |
| WO | 2008/114234 | A2 | 9/2008 |
| WO | 2009/149146 | A1 | 12/2009 |
| WO | 2011044562 | A1 | 4/2011 |
| WO | 2011/090862 | A2 | 7/2011 |
| WO | 2015027166 | A2 | 2/2015 |

OTHER PUBLICATIONS

European Search Report dated Apr. 3, 2017, issued in EP Application No. 14756981.
European Office Action dated Oct. 26, 2016, issued in EP Application No. 14756981.
Chinese Office Action dated Jan. 3, 2017, issued in Chinese Application No. 2014800115910.
European Search Report EP 12191639.9 dated Feb. 20, 2013.
European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
Japanese Office Action dated Nov. 29, 2017, issued in JP Application No. 2015560303.
Japanese Office Action dated Jun. 7, 2018 in JP Appln. No. 2015560303.

* cited by examiner

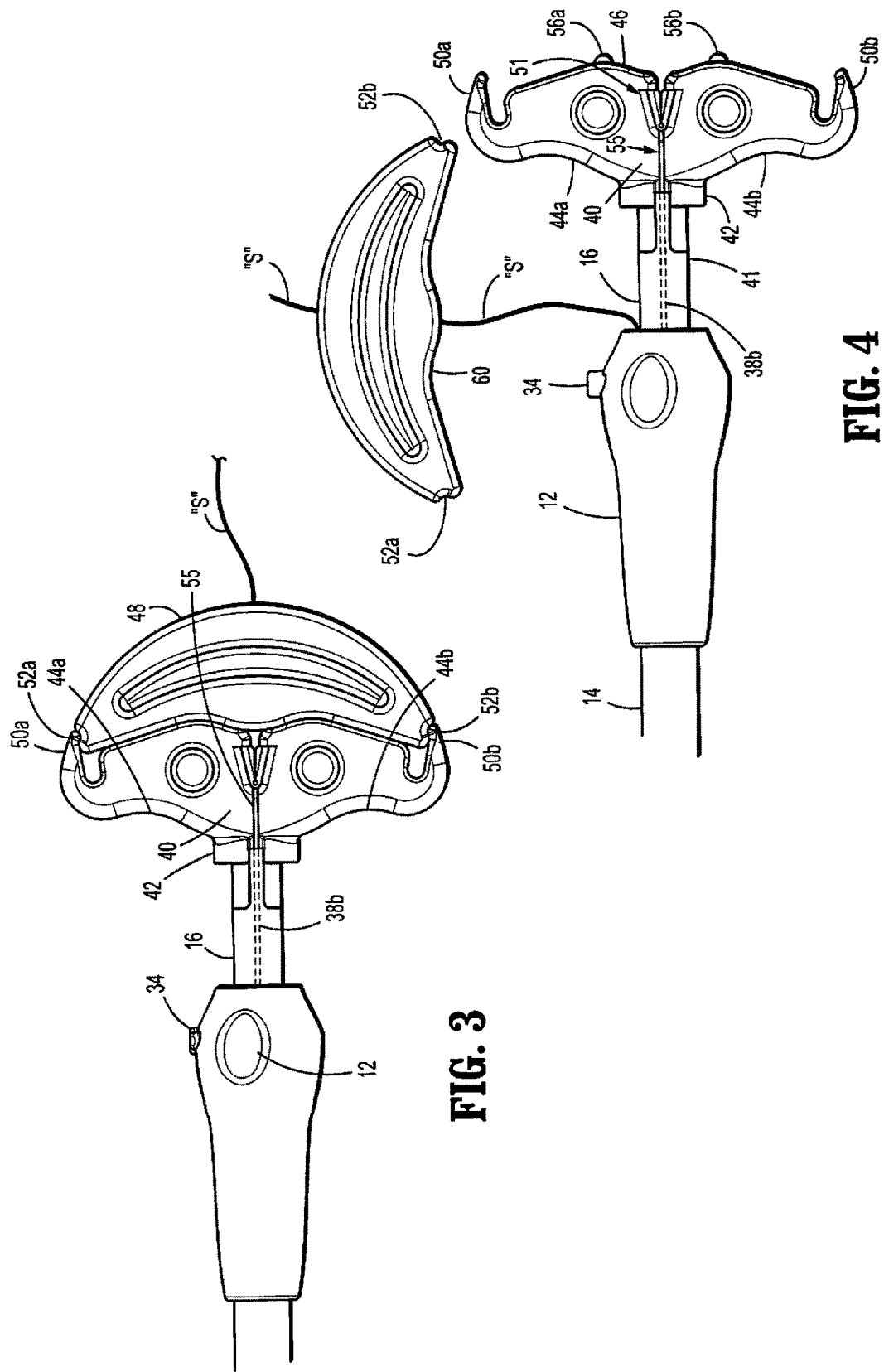

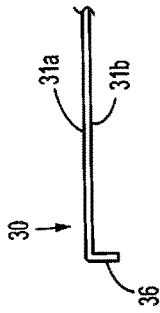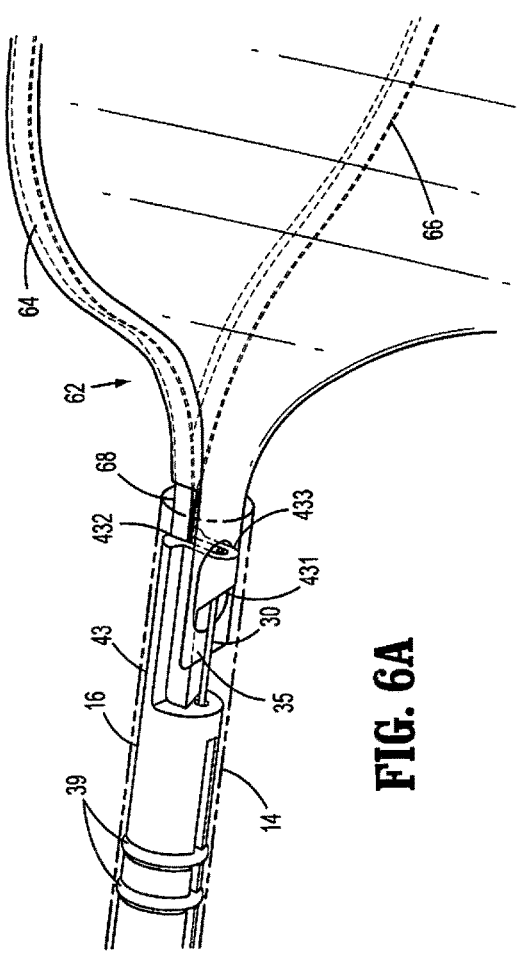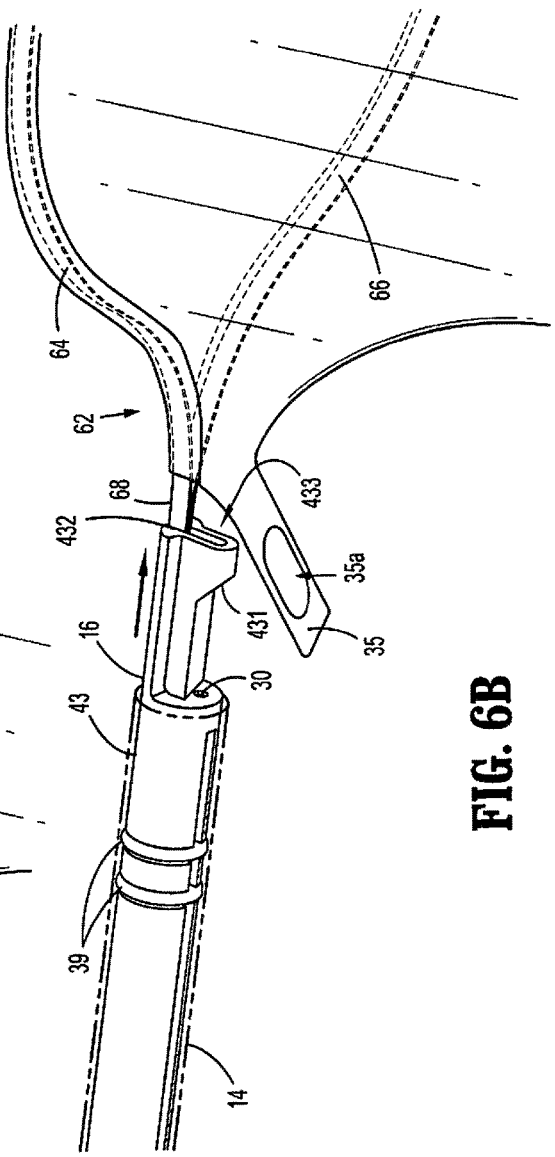

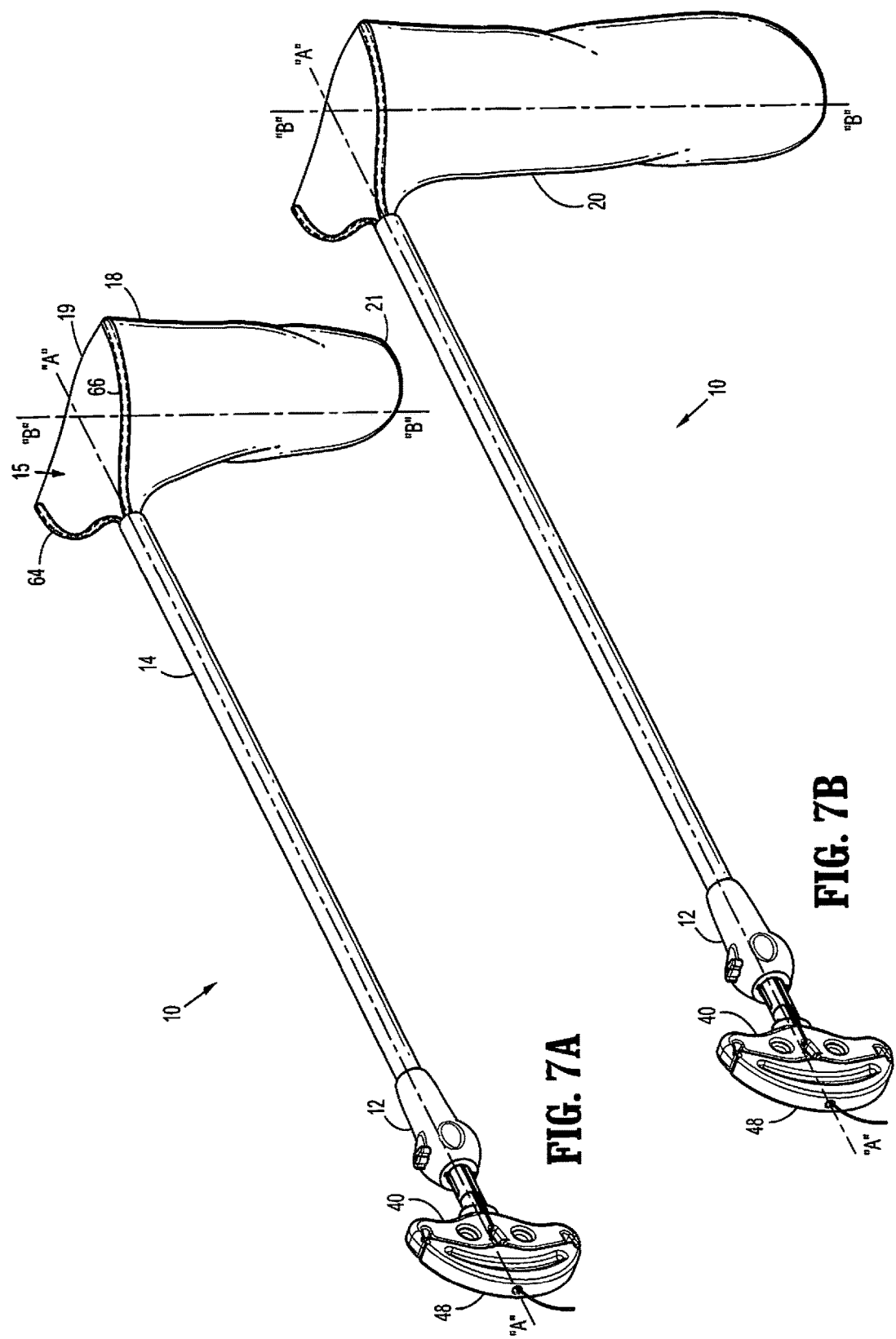

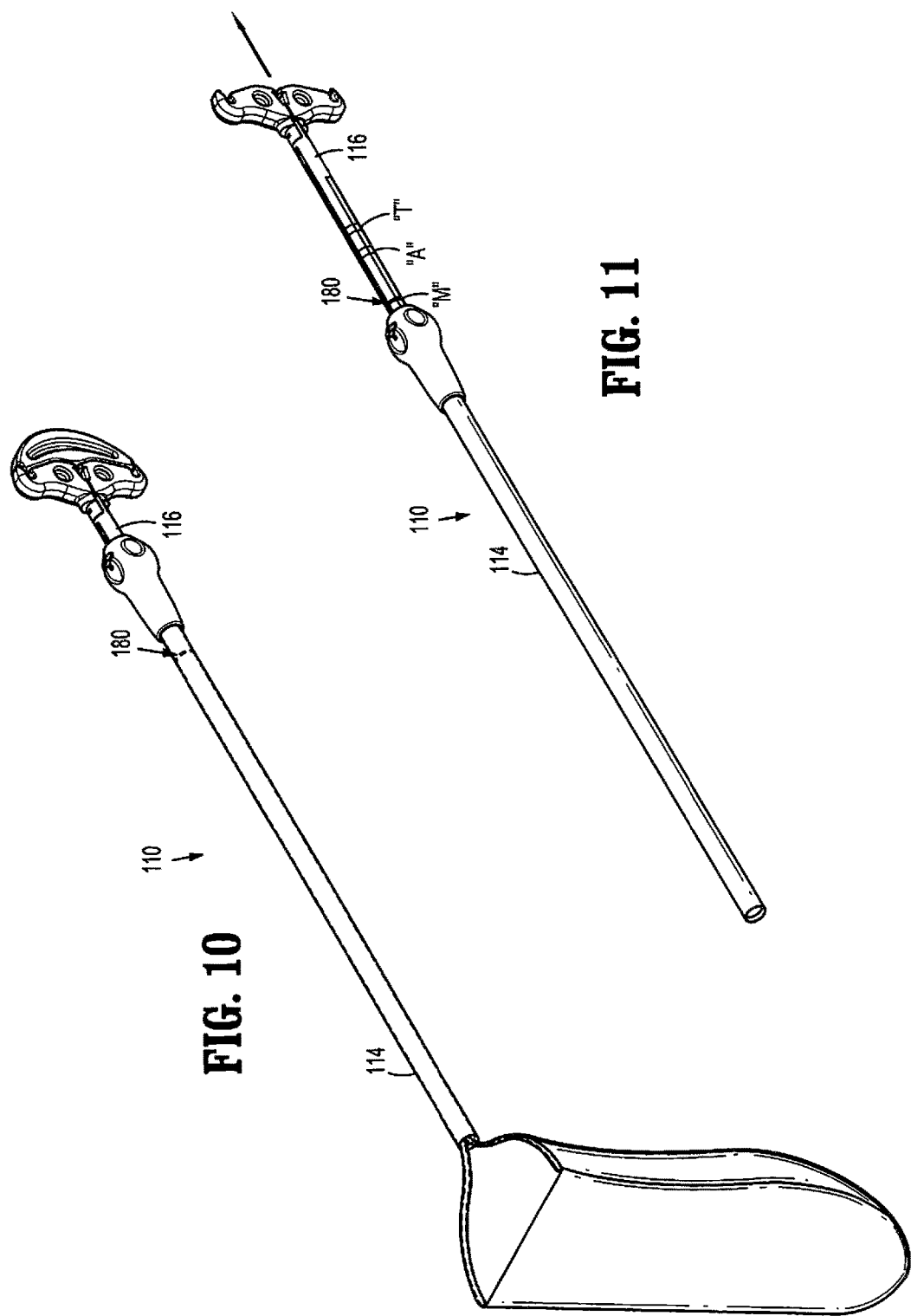

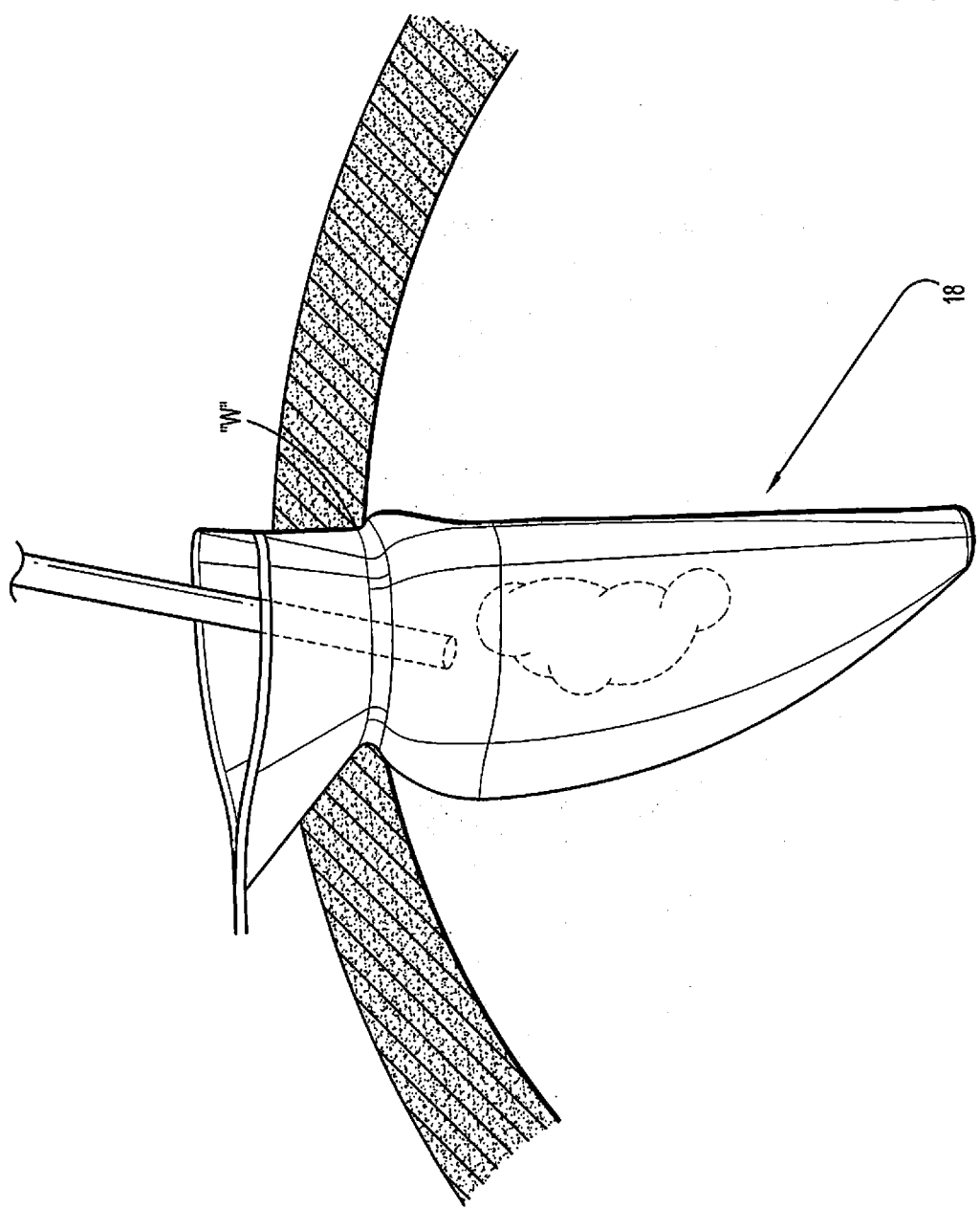

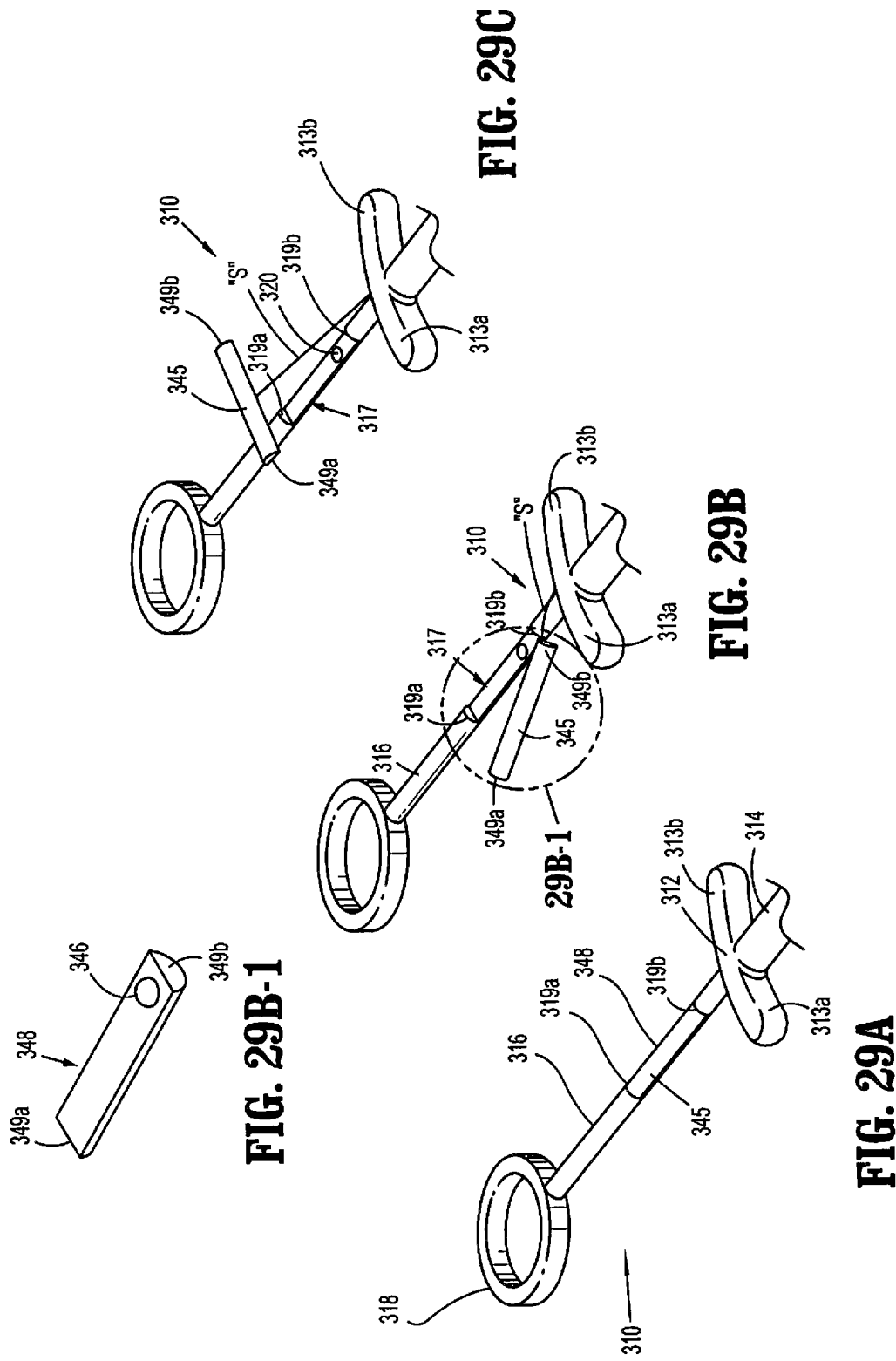

SPECIMEN RETRIEVAL DEVICE WITH POUCH STOP

CROSS-REFERENCE TO RELATED APPLICATIONS

This application is a National Stage Application of PCT/US14/18959 under 35 USC § 371 (a), which claims priority of U.S. Provisional Patent Application Ser. No. 61/771,156 filed Mar. 1, 2013, which claims priority of U.S. Provisional Patent Application Ser. No. 61/771,152 filed Mar. 1, 2013, which claims priority of U.S. Provisional Patent Application Ser. No. 61/771,148 filed Mar. 1, 2013, which claims priority of U.S. Provisional Patent Application Ser. No. 61/771,144 filed Mar. 1, 2013, which claims priority of U.S. Provisional Patent Application Ser. No. 61/771,139 filed Mar. 1, 2013, which claims priority of U.S. Provisional Patent Application Ser. No. 61/771,138 filed Mar. 1, 2013, which claims priority of U.S. Provisional Patent Application Ser. No. 61/771,135 filed Mar. 1, 2013, which claims priority of U.S. Provisional Patent Application Ser. No. 61/771,132 filed Mar. 1, 2013, which claims priority of U.S. Provisional Patent Application Ser. No. 61/771,130 filed Mar. 1, 2013, which claims priority of U.S. Provisional Patent Application Ser. No. 61/771,129 filed Mar. 1, 2013, which claims priority of U.S. Provisional Patent Application Ser. No. 61/771,122 filed Mar. 1, 2013, which claims priority of U.S. Provisional Patent Application Ser. No. 61/771,120 filed Mar. 1, 2013, the disclosures of each of the above-identified applications are hereby incorporated by reference in their entirety.

BACKGROUND

Technical Field

The present disclosure relates to specimen retrieval devices. More particularly, the present disclosure relates to specimen retrieval devices including a selectively detachable pouch.

Background of Related Art

Laparoscopic and endoscopic surgical procedures are minimally invasive procedures in which operations are carried out within the body by means of elongated instruments inserted through small entrance or access openings in the body, e.g., an opening defined by a natural passageway of the body, an opening created by a tissue piercing instrument (e.g., a trocar), etc.

Minimally invasive procedures are often used to partially or totally remove body tissue or organs from the interior of the body, e.g. nephrectomy, cholecystectomy, duodenectomy, ileectomy, jejunectomy and other such procedures. During such procedures, it is common that affected tissue or organs are removed from the patient's body. Various types of entrapment devices are known in the art to facilitate this procedure.

Conventional entrapment devices typically include an elongated applicator including a handle at a proximal end that is operable to deploy a pouch or other suitable device from a distal end of the applicator. The pouch may be perforated and releasably coupled to a spring member along the perforations. As a result of the perforations on the pouch, the pouch may be detached from the spring member by tearing along the perforations.

SUMMARY

Specimen retrieval devices in accordance with the present disclosure include a pouch that is selectively detachable from the device.

In embodiments specimen retrieval devices in accordance with the present disclosure include a housing and an outer shaft connected to the housing and extending distally therefrom. The outer shaft defines a bore therethrough and has an inner shaft slidingly disposed within the bore. The inner shaft has a pouch retention mechanism for connecting a pouch to the inner shaft. A first stop mechanism associated with the housing and is configured to prevent the inner shaft from sliding distally relative to the outer shaft past a first longitudinal position. A first stop mechanism actuator can be actuated to disengage the first stop mechanism so as to enable the inner shaft to slide distally relative to the outer shaft past the first longitudinal position and to cause the pouch retention mechanism to engage a second stop mechanism associated with the housing that allows continued distal movement of the inner shaft relative to the outer shaft past the first longitudinal position, but to prevent distal movement of the pouch retention mechanism past the first longitudinal position. Continued distal sliding of the inner shaft past the first longitudinal position causes the pouch retention mechanism to move proximally relative to the inner shaft to a position at which the pouch is disconnectable from the inner shaft.

In various embodiments, the pouch retention mechanism may include a pin that extends distally within a groove that extends longitudinally along the outer surface of the inner shaft. The pin may include at its proximal end a radially-extending tip that is configured to engage the second stop mechanism of the housing. The first stop mechanism may include a leaf spring that is seated within a groove extends longitudinally along the outer surface of the inner shaft. The actuator may be a spring loaded push-button configured to move the leaf spring out of engagement with the housing. The pouch may include an aperture through which the pouch retention mechanism extends. The inner shaft may include a notch near its distal end, the pouch retention mechanism extending fully across the notch such that the pouch remains attached to the pouch retention mechanism when the inner shaft is proximal of the first longitudinal position relative to the outer shaft. When the pouch retention mechanism is moved proximally relative to the inner shaft, a distal end of the pouch retention mechanism may be retracted such that the pouch retention mechanism no longer extends fully across the notch, thereby allowing the pouch retention mechanism to slide out of engagement with the aperture of the pouch and the pouch to be disconnected from the pouch retention mechanism.

In various embodiments, the specimen retrieval device may also include a pouch support mechanism that is connected to the inner shaft and configured to support the pouch. The pouch support mechanism may include a pair of resilient forks. The pouch may include a slot around the circumference of the mouth of the pouch, and the pair of forks of the pouch support mechanism may be configured to reside within the slots when the pouch is connected to the inner shaft and to be withdrawn out of the slots when the pouch is disconnected from the inner shaft.

Also, the specimen retrieval device may further include a cinch which also resides in the slot around the circumference of the mouth of the pouch. The cinch may be connected at its proximal end to a cinch puller, the cinch puller being configured, when pulled by a user, to cause the mouth of the pouch to close. The cinch may be a suture, a thread, a wire or a cable.

In embodiments, specimen retrieval devices in accordance with the present disclosure include an outer shaft defining a bore therethrough and an inner shaft slidingly disposed within the bore of the outer shaft. The inner shaft has a handle portion at its proximal end. A pouch selectively connected to the inner shaft includes a slot around the circumference of the mouth of the pouch; a cinch that resides in the slot around the circumference of the mouth of the pouch. A cinch puller connected to a proximal end of the cinch is configured, when pulled, to cause the mouth of the pouch to close. Together, the cinch puller and the handle portion of the inner shaft form a complete handle that is grippable by a user.

In embodiments, the cinch puller and the handle portion of the inner shaft may be initially attached to each other, and may be selectively detachable from each other by a user. The cinch may be a suture, a thread, a wire or a cable. The cinch may extend within a groove that extends longitudinally along an outer surface of the inner shaft. The cinch puller may be configured to releasably couple to the handle portion of the inner shaft by detents on a first one of the cinch puller and the handle portion, the detents engaging corresponding indents on a second one of the cinch puller and the handle portion. Also, the handle portion may include at least one cutting mechanism that is configured to cut the cinch.

In various embodiments, the specimen retrieval device may also include a pouch support mechanism connected to the inner shaft and configured to support the pouch. The pouch support mechanism may include a pair of resilient forks. The pair of forks of the pouch support mechanism may be configured to reside within the slots when the pouch is connected to the inner shaft and to be withdrawn out of the slots when the pouch is disconnected from the inner shaft.

In embodiments, specimen retrieval devices in accordance with the present disclosure include an outer shaft defining a bore therethrough and an inner shaft is slidably disposed within the bore of the outer shaft. A pouch is supported by a pouch support mechanism at the distal end of the inner shaft. The inner shaft also includes at least one indication mechanism thereon that is configured to indicate to a user when the pouch support mechanism is retracted to a position at which the pouch support mechanism is fully within the outer shaft.

In embodiments, when the at least one indication mechanism indicates that the pouch support mechanism is retracted to a position at which the pouch support mechanism is fully within the outer shaft, a portion of the pouch may remain outside of the outer shaft. With such an arrangement, a user may repeatedly pull the pouch support mechanism into and out of the outer shaft—the pouch support mechanism being outside of the outer shaft when filling the pouch with tissue and the pouch support mechanism being inside the outer shaft in between such filling steps in a way that ensures that the contents of the pouch will not spill out of the mouth of the pouch.

In embodiments, the at least one indication mechanism may be indicia that are visible to user when the pouch support mechanism is retracted to a position at which the pouch support mechanism is fully within the outer shaft, e.g., the indicia may be at least one marking on the inner shaft. The at least one indication mechanism may also be structure that provides an audible sound to a user when the pouch support mechanism is retracted to a position at which the pouch support mechanism is fully within the outer shaft. Also, the at least one indication mechanism may be a structure that provides tactile feedback to a user when the pouch support mechanism is retracted to a position at which the pouch support mechanism is fully within the outer shaft. The pouch may be releasably supported by the pouch support mechanism.

In accordance with another aspect of the present disclosure, specimen retrieval devices include an outer shaft defining a longitudinal axis and defining a bore therethrough. An inner shaft is slidably disposed within the bore of the outer shaft and pouch is supported at the distal end of the inner shaft. The pouch has a proximal edge that forms an obtuse angle relative to the longitudinal axis of the outer shaft such that the proximal force required to be exerted by a user on the inner shaft relative to the outer shaft in order to pull the pouch into the outer shaft is reduced.

In embodiments, the inner shaft may have a pouch support mechanism at its distal end, the pouch being supported by the pouch support mechanism. The pouch may be releasably supported by the pouch support mechanism. The pouch may include a slot around the circumference of the mouth of the pouch.

Also, the specimen retrieval device may also include a cinch that resides in the slot around the circumference of the mouth of the pouch. The specimen retrieval device may also include a cinch puller connected to a proximal end of the cinch and being configured, when pulled, to cause the mouth of the pouch to close. The cinch may be one of a suture, a thread, a wire or a cable. The cinch may reside within a groove that extends longitudinally along an outer surface of the inner shaft.

In embodiments, the specimen retrieval device may also include a pouch support mechanism connected to the inner shaft and configured to support the pouch. The pouch support mechanism may include a pair of resilient forks, and the pair of forks may be configured to reside within the slots when the pouch is connected to the inner shaft and to be withdrawn out of the slots when the pouch is disconnected from the inner shaft.

In embodiments, the proximal edge may have a curved profile. The proximal edge of the pouch gradually may become closer to being orthogonal relative to the longitudinal axis near to the bottom of the pouch. The proximal edge of the pouch may define a concave curvature at or near a mouth of the pouch and defines a convex curvature at or near a bottom portion of the pouch. In addition, the mouth of the pouch may form a compound angle so as to provide an increased area during use for a specimen to be received, as well as to provide the mouth to a user at an angle that is most conducive to receiving the specimen.

In embodiments, specimen retrieval devices in accordance with the present disclosure include an outer shaft defining a longitudinal axis and defining a bore therethrough. An inner shaft is slidably disposed within the bore of the outer shaft. A pouch supported at the distal end of the inner shaft has a mouth including a compound angle which, during use, is open for receiving a tissue specimen. The pouch may include a proximal edge that forms an obtuse angle relative to the longitudinal axis of the outer shaft such that the proximal force required to be exerted by a user on the inner shaft relative to the outer shaft in order to pull the pouch into the outer shaft is reduced. The inner shaft may have a pouch support mechanism at its distal end to support the pouch. The pouch may be releasably supported by the pouch support mechanism.

In embodiments, the pouch may include a slot around the circumference of a mouth of the pouch. The specimen retrieval device may also include a cinch that resides in the slot around the circumference of the mouth of the pouch. The specimen retrieval device may also include a cinch puller connected to a proximal end of the cinch and being configured, when pulled, to cause the mouth of the pouch to close. The cinch may be one of a suture, a thread, a wire or a cable. The cinch may reside within a groove that extends longitudinally along an outer surface of the inner shaft. The pouch support mechanism may include a pair of resilient forks. The pair of forks of the pouch support mechanism may be configured to reside within slots around the mouth of the pouch when the pouch is connected to the inner shaft and to be withdrawn out of the slots when the pouch is disconnected from the inner shaft. The proximal edge of the pouch may have a curved profile.

In embodiments, specimen retrieval devices in accordance with the present disclosure include an outer shaft defining a longitudinal axis and defining a bore therethrough and an inner shaft slidably disposed within the bore of the outer shaft. A pouch supported at the distal end of the inner shaft has an open mouth and a closed end opposite the mouth. The pouch further has a waist at a position between the mouth and the closed end. The inner shaft may have a pouch support mechanism at its distal end to support the pouch. The pouch may be releasably supported by the pouch support mechanism. The pouch may include a slot around the circumference of the mouth of the pouch.

In various embodiments, the specimen retrieval device may also include a cinch that resides in the slot around the circumference of the mouth of the pouch. In addition, the specimen retrieval device may also include a cinch puller connected to a proximal end of the cinch and being configured, when pulled, to cause the mouth of the pouch to close. The cinch may be one of a suture, a thread, a wire or a cable. The cinch may reside within a groove that extends longitudinally along an outer surface of the inner shaft.

In various embodiments, the specimen retrieval device may also include a pouch support mechanism connected to the inner shaft and configured to support the pouch. The pouch support mechanism may include a pair of resilient forks. The pair of forks of the pouch support mechanism may be configured to reside within the slots when the pouch is connected to the inner shaft and to be withdrawn out of the slots when the pouch is disconnected from the inner shaft.

Also, the proximal edge of the pouch may have a curved profile. The proximal edge of the pouch may gradually become closer to being orthogonal relative to the longitudinal axis near to the bottom of the pouch. The proximal edge of the pouch may define a concave curvature at or near a mouth of the pouch and may define a convex curvature at or near a bottom portion of the pouch.

During a surgical procedure, the mouth of the pouch may be configured to be positioned outside of a surgical site, the waist of the pouch may be configured to reside within an incision, and the closed end of the pouch may be configured to be positioned inside of the surgical site. The waist may have a dimension in a radial direction that is less than the radial dimension of the mouth of the pouch.

In embodiments, specimen retrieval devices in accordance with the present disclosure include an outer shaft defining a bore therethrough and an inner shaft slidingly disposed within the bore of the outer shaft. A pouch is connected to the inner shaft by a pouch retention mechanism on the inner shaft. The pouch retention mechanism permits selective detachment of the pouch from the inner shaft while the pouch retention mechanism is within the outer shaft.

The pouch retention mechanism may include at least one member that moves longitudinally along an outer surface of the inner shaft. The at least one member may move by sliding relative to the inner shaft. The at least one member may have a finger structure. The at least one member and the inner shaft may also include corresponding features that prevent the at least one member and the inner shaft from inadvertently moving relative to each other. The pouch may include one or more openings through which the pouch retention mechanism extends.

In embodiments, the inner shaft may include one or more protrusions near its distal end. The at least one member may abut the one or more protrusions such that the pouch remains attached to the one or more protrusions when the at least one member is in a proximal position relative to the inner shaft. When the at least one member is moved proximally relative to the inner shaft, a distal end of the at least one member is retracted such that the at least one member no longer abuts the one or more protrusions. This may allow the one or more protrusions to slide out of engagement with the opening of the pouch and the pouch to be disconnected from the pouch retention mechanism.

In addition, the specimen retrieval device may also include a pouch support mechanism connected to the inner shaft and configured to support the pouch. The pouch support mechanism may include a pair of resilient forks. The pouch may include a slot around the circumference of the mouth of the pouch. The pair of forks of the pouch support mechanism may be configured to reside within the slots when the pouch is connected to the inner shaft and to be withdrawn out of the slots when the pouch is disconnected from the inner shaft.

In embodiments, the specimen retrieval device may also include a cinch. The cinch may also reside in the slot around the circumference of the mouth of the pouch. The cinch may be connected at its proximal end to an actuator. The actuator may be configured, when actuated, to pull the cinch a first distance so as to move the at least one member proximally relative to the inner shaft. The cinch may also be configured, when pulled proximally a second distance, to cause the mouth of the pouch to close. The cinch may be one of a suture, a thread, a wire or a cable.

In embodiments, specimen retrieval devices in accordance with the present disclosure include an outer shaft defining a bore therethrough and an inner shaft slidingly disposed within the bore of the outer shaft. The inner shaft has a handle and a pouch retention mechanism connecting a pouch to the inner shaft. An actuator movably connected to the handle actuates the pouch retention mechanism to permit a user to selectively detach the pouch from the inner shaft. The actuator may be a ring and may be pivotably connected to the handle. The handle may define a void, the ring having a portion that extends radially into the void so as to provide a surface for a user's finger to pivot the ring relative to the handle.

In embodiments, the specimen retrieval device also includes a cinch connected at its proximal end to the actuator The actuator may be configured, when actuated, to pull the cinch a first distance so as to move the pouch retention mechanism proximally relative to the inner shaft. The cinch may be one of a suture, a thread, a wire or a cable.

The specimen retrieval device may also include a pouch support mechanism connected to the inner shaft and configured to support the pouch. The pouch support mechanism may include a pair of resilient forks. The pouch may include a slot around the circumference of the mouth of the pouch. The pair of forks of the pouch support mechanism may be configured to reside within the slots when the pouch is connected to the inner shaft and to be withdrawn out of the slots when the pouch is disconnected from the inner shaft. The cinch may also reside in the slot around the circumference of the mouth of the pouch. The cinch may also be configured such that, when pulled proximally a second distance, it causes the mouth of the pouch to close.

In various embodiments, the pouch retention mechanism may include at least one member that moves longitudinally along an outer surface of the inner shaft. The at least one member may move by sliding relative to the inner shaft. The pouch may include one or more openings through which the pouch retention mechanism extends. The inner shaft may include one or more protrusions near its distal end. The at least one member may abut the one or more protrusions such that the pouch remains attached to the one or more protrusions when the at least one member is in a proximal position relative to the inner shaft. In such an arrangement, when the at least one member is moved proximally relative to the inner shaft by actuation of the actuator, a distal end of the at least one member may be retracted such that the at least one member no longer abuts the one or more protrusions, thereby allowing the one or more protrusions to slide out of engagement with the opening of the pouch and the pouch to be disconnected from the pouch retention mechanism.

In embodiments, specimen retrieval devices in accordance with the present disclosure include an outer shaft defining a bore and an inner shaft slidably disposed within the bore of the outer shaft. A pouch is detachably coupled to a distal end of the inner shaft. A pouch retention mechanism is configured to selectively retain the pouch at the distal end of the inner shaft. Retraction of the pouch retention mechanism allows the pouch to be detached from the inner shaft.

The pouch retention mechanism may be retracted by engagement of the pouch retention mechanism with at least one stop disposed on the outer shaft. The pouch retention mechanism may be a retention pin including a proximal end that is configured to engage the at least one stop. The pouch retention mechanism may be a retention pin that is retracted by a user pulling the retention pin in a proximal direction relative to the inner shaft. The retention pin may be attached to a cinch that is configured to be retracted by a user in a proximal direction relative to the inner shaft.

In embodiments, the pouch may include an aperture through which the pouch retention mechanism extends. The inner shaft may include a notch near its distal end, the pouch retention mechanism extending fully across the notch when the pouch retention mechanism is in a distal position relative to the inner shaft whereby the pouch remains attached to the pouch retention mechanism. When the pouch retention mechanism is moved proximally relative to the inner shaft, a distal end of the pouch retention mechanism may be retracted such that the pouch retention mechanism no longer extends fully across the notch, thereby allowing the pouch retention mechanism to slide out of engagement with the aperture of the pouch and the pouch to be disconnected from the pouch retention mechanism.

The specimen retrieval device may also include a pouch support mechanism connected to the inner shaft and configured to support the pouch. The pouch support mechanism may include a pair of resilient forks. The pouch may include a slot around the circumference of the mouth of the pouch, and the pair of forks of the pouch support mechanism may be configured to reside within the slots when the pouch is connected to the inner shaft and to be withdrawn out of the slots when the pouch is disconnected from the inner shaft.

The specimen retrieval device may also include a cinch which also resides in the slot around the circumference of the mouth of the pouch. The cinch may be connected at its proximal end to a cinch handle, the cinch handle being configured, when pulled, to cause the mouth of the pouch to close. The cinch may be one of a suture, a thread, a wire or a cable.

In embodiments, specimen retrieval devices in accordance with the present disclosure include a housing and an outer shaft connected to the housing and extending distally therefrom. The outer shaft defines a bore therethrough and an inner shaft is slidingly disposed within the bore of the outer shaft. A pouch is connected to the inner shaft. A cinch handle is detachably mounted on the inner shaft. The cinch handle prevents the inner shaft from sliding distally relative to the outer shaft past a first longitudinal position. When the cinch handle is detached from the inner shaft, the inner shaft is allowed to slide distally relative to the outer shaft past the first longitudinal position.

In embodiments, the inner shaft may have a pouch retention mechanism. The pouch may be connected to the inner shaft by the pouch retention mechanism. The pouch retention mechanism may be configured to retain the pouch to the inner shaft when the inner shaft is in a position relative to the outer shaft that is proximal to the first longitudinal position, and the pouch retention mechanism may be configured to allow the pouch to be detached from the inner shaft when the inner shaft is in a position relative to the outer shaft that is distal to the first longitudinal position. The pouch retention mechanism may be retracted by engagement of the pouch retention mechanism with at least one stop disposed on the outer shaft. The pouch retention mechanism may be a retention pin including a proximal end that is configured to engage the at least one stop. The pouch retention mechanism may be a retention pin that is retracted by a user pulling the retention pin in a proximal direction relative to the inner shaft. The retention pin may be attached to a cinch that is configured to be retracted by a user in a proximal direction relative to the inner shaft. The cinch may be connected at its proximal end to the cinch handle, such that, when the cinch handle is retracted by a user in a proximal direction relative to the inner shaft, the retention pin is also retracted by a user in a proximal direction relative to the inner shaft.

The pouch may include an aperture through which the pouch retention mechanism extends. The inner shaft may include a notch near its distal end, the pouch retention mechanism extending fully across the notch when the pouch retention mechanism is in a distal position relative to the inner shaft whereby the pouch remains attached to the pouch retention mechanism by the aperture. When the pouch retention mechanism is moved proximally relative to the inner shaft, a distal end of the pouch retention mechanism may be retracted such that the pouch retention mechanism no longer extends fully across the notch, thereby allowing the pouch retention mechanism to slide out of engagement with the aperture of the pouch and the pouch to be disconnected from the pouch retention mechanism.

The specimen retrieval device may also include a pouch support mechanism connected to the inner shaft and configured to support the pouch. The pouch support mechanism may include a pair of resilient forks. The pouch may include a slot around the circumference of the mouth of the pouch, and the pair of forks of the pouch support mechanism may be configured to reside within the slots when the pouch is connected to the inner shaft and to be withdrawn out of the slots when the pouch is disconnected from the inner shaft.

In embodiments, the specimen retrieval device may also include a cinch which also resides in the slot around the circumference of the mouth of the pouch. The cinch may be connected at its proximal end to the cinch handle, the cinch handle being configured, when pulled, to cause the mouth of the pouch to close. The cinch may be one of a suture, a thread, a wire or a cable.

In embodiments, specimen retrieval devices in accordance with the present disclosure include a housing and an outer shaft coupled to and extending distally from the housing. A inner shaft is disposed within the outer shaft and movable relative thereto. The inner shaft includes a pair of resilient members at a distal end thereof and a handle assembly at a proximal end thereof. A pouch is releasably coupled to the pair of resilient members. A retention pin is configured to selectively engage the pouch. A cinch includes a proximal end removably coupled to the handle of the inner shaft and a distal end coupled to the pouch and is configured to releasably couple to the retention pin. Engagement between a proximal end of the housing and the handle assembly uncouples the pouch from the retention pin and allows the pouch to uncouple from the pair of resilient members when the inner shaft is moved proximally into the outer shaft.

The retention pin may include an elongated configuration including proximal and distal ends and at least partially extends within the outer shaft. The proximal end of the retention pin may include a generally arcuate configuration that is configured to engage the proximal end of the housing to limit distal translation of the retention pin. The proximal end of the retention pin may include at least one mechanical interface thereon that is configured to engage a corresponding at least one mechanical interface that is disposed within the outer shaft to limit distal translation of the retention pin. The distal end of the cinch my include a distal loop that secures to the distal end of the retention pin for securing the pouch to the retention pin and may include a proximal loop that is configured to be grasped by a user for cinching the pouch. A distal end of the proximal loop may be configured to releasably couple to the handle assembly of the inner shaft.

The handle assembly may include at least one cutting mechanism that is configured to cut the cinch. The proximal end may be configured to engage one of the proximal ends of the outer shaft and at least one mechanical interface disposed within the outer shaft.

In embodiments, specimen retrieval devices in accordance with the present disclosure include a housing, an outer shaft connected to the housing and extending distally therefrom, and an inner shaft slidingly disposed within a bore defined through the outer shaft. A pouch is connected to the inner shaft. A cinch handle is movably coupled to the inner shaft. When the inner shaft is in a first longitudinal position relative to the outer shaft, the cinch handle is positioned within the outer shaft and is inaccessible to a user, and when the inner shaft is in a second longitudinal position relative to the outer shaft, the cinch handle is positioned outside of the outer shaft and is accessible to a user.

The inner shaft may have a pouch retention mechanism. The pouch may be connected to the inner shaft by the pouch retention mechanism. The pouch retention mechanism may be configured to retain the pouch to the inner shaft when the inner shaft is in the first longitudinal position relative to the outer shaft, and the pouch retention mechanism may be configured to allow the pouch to be detached from the inner shaft when the inner shaft is in the second longitudinal position relative to the outer shaft. The pouch retention mechanism may be retracted by engagement of the pouch retention mechanism with at least one stop disposed on the outer shaft. The pouch retention mechanism may be a retention pin including a proximal end that is configured to engage the at least one stop. The pouch retention mechanism may be a retention pin that is retracted by a user pulling the retention pin in a proximal direction relative to the inner shaft.

The retention pin may be attached to a cinch that is configured to be retracted by a user in a proximal direction relative to the inner shaft. The cinch may be connected at its proximal end to the cinch handle, such that, when the cinch handle is retracted by a user in a proximal direction relative to the inner shaft, the retention pin is also retracted by a user in a proximal direction relative to the inner shaft. The pouch may include an aperture through which the pouch retention mechanism extends.

The inner shaft may include a notch near its distal end, the pouch retention mechanism extending fully across the notch when the pouch retention mechanism is in a distal position relative to the inner shaft whereby the pouch remains attached to the pouch retention mechanism by the aperture. When the pouch retention mechanism is moved proximally relative to the inner shaft, a distal end of the pouch retention mechanism may be retracted such that the pouch retention mechanism no longer extends fully across the notch, thereby allowing the pouch retention mechanism to slide out of engagement with the aperture of the pouch and the pouch to be disconnected from the pouch retention mechanism.

The specimen retrieval device may also include a pouch support mechanism connected to the inner shaft and configured to support the pouch. The pouch support mechanism may include a pair of resilient forks. The pouch may include a slot around the circumference of the mouth of the pouch, and the pair of forks of the pouch support mechanism may be configured to reside within the slots when the pouch is connected to the inner shaft and to be withdrawn out of the slots when the pouch is disconnected from the inner shaft.

The specimen retrieval device may also include a cinch which also resides in the slot around the circumference of the mouth of the pouch. The cinch may be connected at its proximal end to the cinch handle, the cinch handle being configured, when pulled, to cause the mouth of the pouch to close. The cinch may be one of a suture, a thread, a wire or a cable.

The cinch handle may include a generally elongated configuration including proximal and distal ends having respective tab members. The inner shaft may include at least one pocket having a configuration that complements the elongated configuration of the cinch handle for releasably receiving the cinch handle. The at least one pocket may include corresponding undercuts that are configured to engage the tab members on the cinch handle to secure the cinch handle to the inner shaft. The cinch handle may include at least one detent on an underside thereof, such that the at least one detent seats within a corresponding indent provided within the at least one pocket on the inner shaft, and the at least one detent is pivotable about the at least one indent and configured to facilitate uncoupling the cinch handle from the at least one pocket. The cinch handle may include at least one detent on an underside thereof, the at least one detent press fit into a corresponding indent provided within the at least one pocket on the inner shaft, the at least one detent rotatable about the at least one indent and removable therefrom to facilitate uncoupling the cinch handle from the at least one pocket. The cinch handle may include at least one detent on an underside thereof and a pair of flexible lateral extensions, such that the at least one detent seats within a corresponding indent provided within the at least one pocket on the inner shaft and the lateral extensions are configured to releasably couple to the inner shaft along the at least one pocket to facilitate uncoupling the cinch handle from the at least one pocket.

In embodiments, specimen retrieval devices in accordance with the present disclosure include an outer shaft defining a bore, a pouch, and an inner shaft slidably disposed within the outer shaft. The inner shaft includes a pair of resilient members at a distal end thereof for supporting the pouch. The resilient members include respective distal ends that are configured to nest with one another when pressed against each other. The distal ends may have corresponding curvatures when viewed proximally. The inner shaft may be movable within the outer shaft from an extended configuration at which the resilient members position the pouch to receive tissue to a retracted configuration at which the resilient members are at least partially within the outer shaft. The distal ends may each include an arcuate proximal portion that is configured to facilitate maintaining the distal ends in the nested configuration while the pouch is being deployed from the shaft.

The pouch may be detachably coupled to a distal end of the inner shaft. The specimen retrieval device may also include a pouch retention mechanism configured to detachably connect the pouch to the distal end of the inner shaft. The pouch may include a slot around the circumference of the mouth of the pouch, and the pair of resilient members may be configured to reside within the slots when the pouch is connected to the inner shaft and to be withdrawn out of the slots when the pouch is disconnected from the inner shaft.

The specimen retrieval device may also include a cinch which also resides in the slot around the circumference of the mouth of the pouch. The cinch may be connected at its proximal end to a cinch handle, the cinch handle being configured, when pulled, to cause the mouth of the pouch to close. The cinch may be one of a suture, a thread, a wire or a cable.

BRIEF DESCRIPTION OF THE DRAWINGS

Embodiments of the presently disclosed specimen retrieval device are described hereinbelow with reference to the drawings wherein:

FIG. 3 is a partial, side view of the proximal portion of the specimen retrieval device illustrating a handle assembly and cinch puller coupled to one another;

FIG. 4 is a partial, side view of the proximal portion of the specimen retrieval device illustrating the handle assembly and cinch puller uncoupled from one another;

FIG. 5 is a schematic view of a retention pin associated with the specimen retrieval device;

FIGS. 6A-6B are perspective views of a distal portion of the specimen retrieval device illustrating a "normal use" configuration and a "release" configuration, respectively;

FIGS. 7A-7B are perspective views illustrating the specimen retrieval device depicted in FIG. 1 with respective short and long pouches coupled thereto;

FIG. 10 is of a perspective view of a specimen retrieval device in accordance with another embodiment of the present disclosure with a pouch in a deployed configuration;

FIG. 11 is a perspective view of the specimen retrieval device depicted in FIG. 10 with the pouch in a retracted configuration;

FIG. 12 is a perspective view of a specimen retrieval device in accordance with another embodiment of the present disclosure with a pouch in a deployed configuration;

FIGS. 29A, 29B, and 29C are partial, perspective views of a specimen retrieval device in accordance with still yet another embodiment of the present disclosure with a cinch handle of the specimen retrieval device shown in various positions;

FIG. 29B-1 is an enlarged area of detail shown in FIG. 29B inverted;

DETAILED DESCRIPTION OF THE EMBODIMENTS

Figure 1:
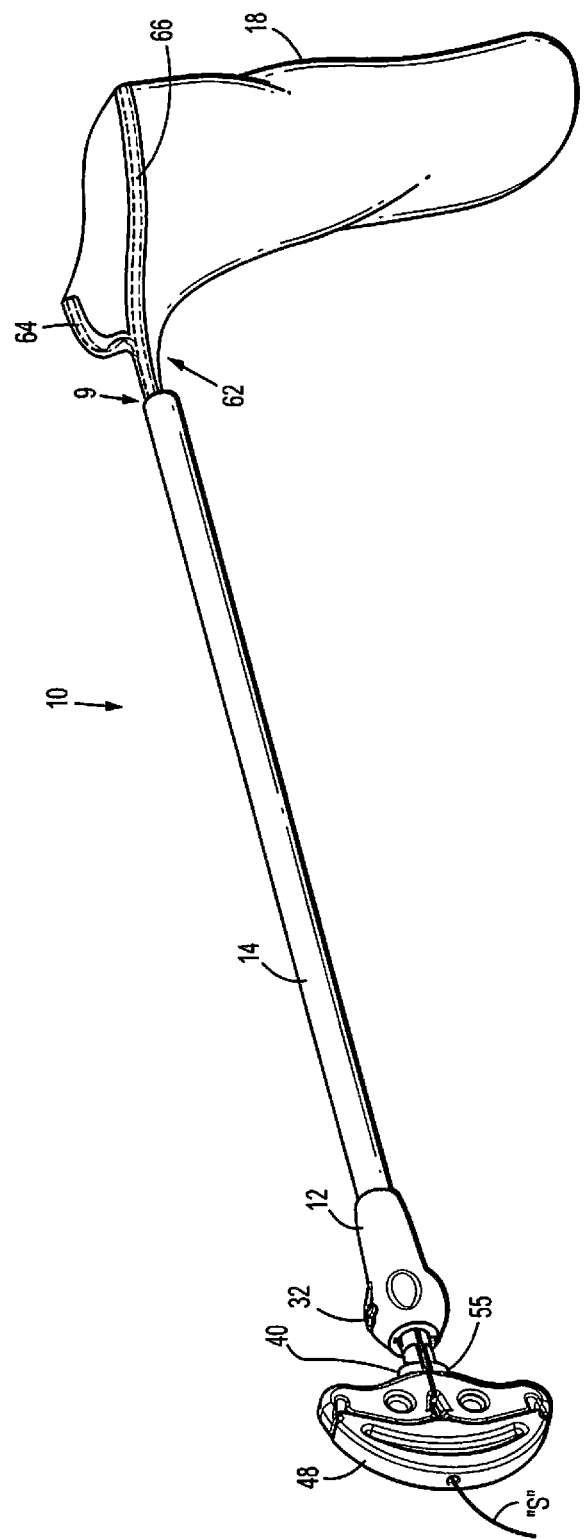
FIG. 1 is a perspective view of a specimen retrieval device in accordance with an embodiment of the present disclosure.

Embodiments of the present disclosure will now be described in detail with reference to the drawings, in which like reference numerals designate identical or corresponding elements in each of the several views. As used herein, the term distal refers to the portion of the instrument which is farthest from the user, while the term proximal refers to that portion of the instrument which is closest to the user. In the following description, well-known functions or constructions are not described in detail to avoid obscuring the present disclosure in unnecessary detail.

As used herein with reference to the present disclosure, the terms laparoscopic and endoscopic are interchangeable and refer to instruments having a relatively narrow operating portion for insertion into a cannula or a small incision in the skin. They also refer to minimally invasive surgical procedures. It is believed that the present disclosure may find use in any procedure where access to the interior of the body is limited to a relatively small incision, with or without the use of a cannula, as in minimally invasive procedures.

Figure 2:
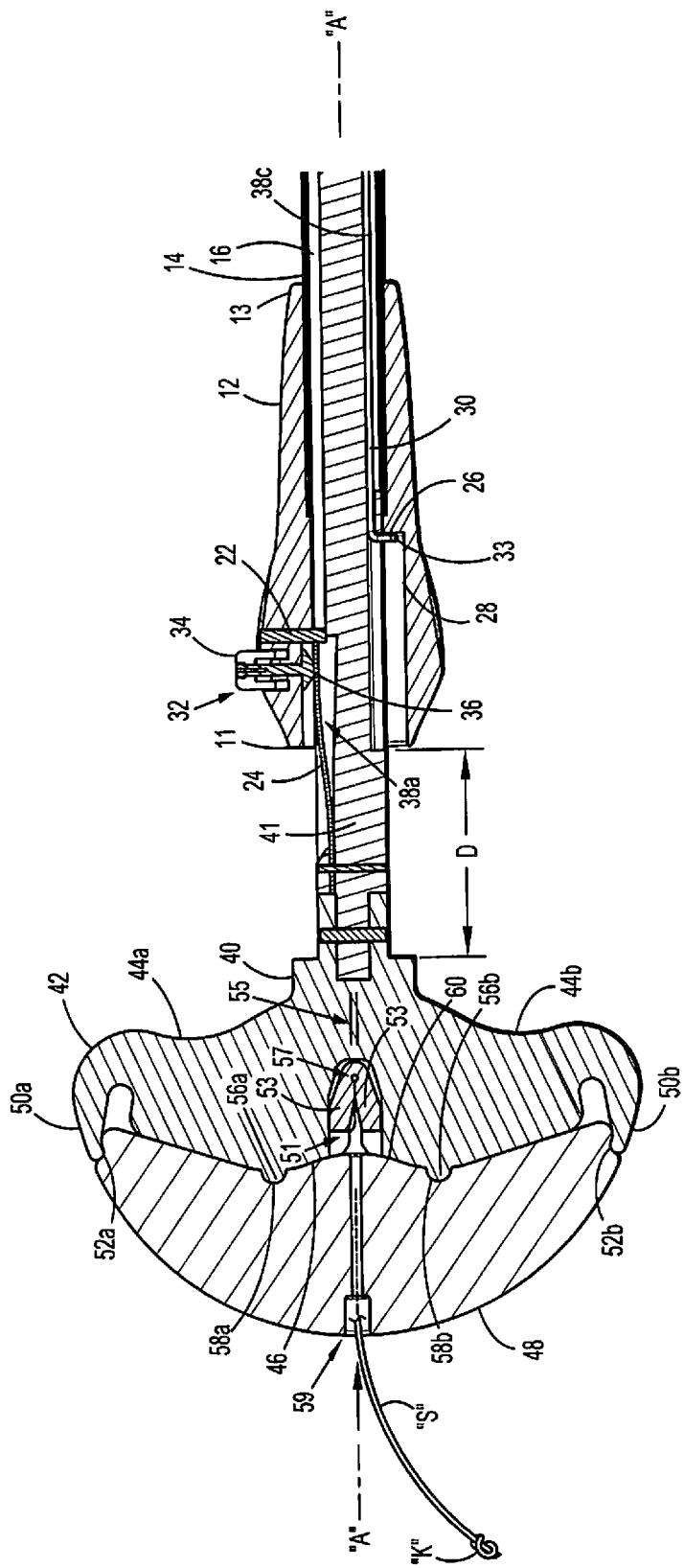
FIG. 2 is a partial, cross-sectional view of a proximal portion of the specimen retrieval device depicted in FIG. 1.

With reference to FIGS. 1-8, and initially with reference to FIG. 1, a specimen retrieval device 10 according to an embodiment of the present disclosure is illustrated. Specimen retrieval device 10 includes a housing 12, an outer shaft 14 and an inner shaft 16 (inner shaft 16 is shown in FIG. 2). Specimen retrieval device 10 (and components associated therewith) may be formed from any suitable biocompatible material, e.g., plastic. In an embodiment, an injection molding manufacturing process may be utilized to form housing 12, outer shaft 14 and inner shaft 16.

Continuing with reference to FIG. 1, housing 12 includes a generally elongated configuration and may be formed as a unitary component or as two separate half components that are coupled to one another by one or more suitable coupling methods (e.g., one or more suitable adhesives). In the latter instance, an indent/detent configuration (not explicitly shown) may be utilized to facilitate coupling the two separate half components. In an assembled configuration, housing 12 may serve as a handle for a user to grasp to facilitate manipulation of specimen retrieval device 10.

Referring to FIG. 2, one or more stops are provided on housing 12 and are configured to engage one or more corresponding release mechanisms that are provided on inner shaft 16. Specifically, a first stop (e.g., a stop pin 22) is provided at a proximal end of housing 12 and is configured to engage a corresponding first release mechanism (e.g., a leaf spring 24) provided at a proximal end of inner shaft 16. In the illustrated embodiment, stop pin 22 is press fit into a recess (not explicitly shown) provided on housing 12 and extends within housing 12 to contact leaf spring 24. Other devices and/or components (e.g., a detent) may be utilized in place of stop pin 22 to engage leaf spring 24. Stop pin 22 is configured to contact leaf spring 24 so as to prevent inner shaft 16 from translating distally past the point at which the leaf spring 24 engages the stop pin 22. Moreover, a second stop (e.g., an inner flange 26 formed along an inner wall 28 of housing 12) is located distally with respect to stop pin 22 and is configured to selectively engage a second release mechanism (e.g., a retention pin 30) that is operably coupled to inner shaft 16. Engagement between retention pin 30 and flange 26 prevents distal translation of retention pin 30 relative to the outer shaft 16 past a predetermined longitudinal position while allowing the inner shaft 16 to continue to move distally relative to the outer shaft 14 so as to allow a pouch 18 to uncouple from inner shaft 16. Accordingly, and unless otherwise noted, the operable components and/or features of specimen retrieval device 10 will be described in terms of use with pouch 18.

Continuing with reference to FIG. 2 and with reference to FIGS. 3-4, an actuation mechanism 32 of suitable configuration is provided at a proximal end of housing 12 and is configured to selectively engage leaf spring 24 to move leaf spring 24 out of engagement with stop pin 22. In the illustrated embodiment, for example, actuation mechanism 32 is in the form of a spring loaded push-button 34 including a contact pad 36 that is configured to contact leaf spring 24 when push-button 34 is depressed. A notch or groove 38a of suitable configuration is provided at a proximal end 41 of inner shaft 16 and is configured to allow leaf spring 24 to pivot therein when push-button 34 is depressed. The depth of groove 38a is adequate to allow leaf spring 24 to translate beneath stop pin 22 as inner shaft 16 is moved distally.

Proximal and distal apertures of suitable configuration (not explicitly shown) are provided at respective proximal and distal ends 11, 13 of housing 12 (FIG. 2). Specifically, the distal aperture of housing 12 is configured to receive a proximal end of outer shaft 14 and the proximal aperture of housing 12 is configured to receive inner shaft 16 therethrough. Since inner shaft 16 is positioned within outer shaft 14 and outer shaft 14 does not extend to the proximal end of housing 12, the proximal aperture of housing 12 may be smaller than the distal aperture of housing 12. The proximal aperture of housing 12 is large enough to allow proximal and distal translation of inner shaft 16 including leaf spring 24 therethrough.

Outer shaft 14 extends distally from housing 12 and includes a generally tubular configuration having a longitudinal axis "A-A" defined therethrough. Longitudinal axis "A-A" is oriented in a different, e.g., a substantially perpendicular or orthogonal direction, with respect to a longitudinal axis "B-B" that is defined through one of the aforementioned pouches (e.g., pouch 18) when pouch 18 is in a deployed state (see FIGS. 7A-7B for example). Outer shaft 14 is dimensioned for insertion through a trocar cannula (or natural body orifice) for endoscopic or laparoscopic procedures. Moreover, an aperture 9 (FIG. 1) of suitable configuration is provided at a distal end of outer shaft 14 and is configured to allow ingress and egress of inner shaft 16 including pouch 18 therethrough. Outer shaft 14 operably couples to housing 12 via one or more suitable coupling methods (e.g., one or more suitable adhesives). Outer shaft 14, however, may be monolithically formed with housing 12.

Figure 9:
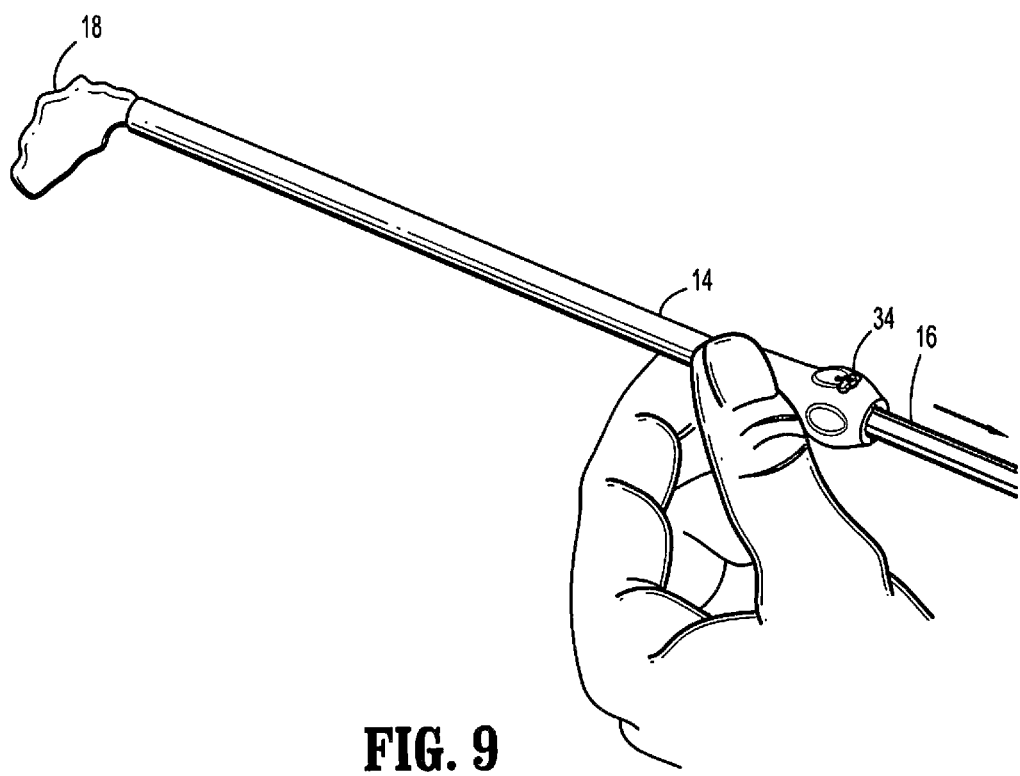
FIG. 9 is a perspective view of the specimen retrieval device depicted in FIG. 1. illustrating the specimen retrieval device being loaded into an outer shaft of the specimen retrieval device for insertion through an access port, or natural orifice of a patient.

Inner shaft 16 includes a generally elongated configuration and is positioned within outer shaft 14. Inner shaft 16 is translatable within outer shaft 14 to move pouch 18 to a retracted configuration wherein pouch 18 is disposed within outer shaft 14 for positioning specimen retrieval device 10 through an access port (FIG. 9 shows pouch 18 in a partially retracted configuration). Moreover, inner shaft 16 may be utilized to move pouch 18 to an extended or deployed configuration wherein pouch 18 is disposed outside of outer shaft 14 for positioning target tissue within pouch 18, see FIGS. 7A-7B for example. Further, inner shaft 16 is translatable to move pouch 18 to a "release" configuration for uncoupling pouch 18 from inner shaft 16. To these ends, a handle assembly 40 is provided at proximal end 41 of inner shaft 16 and is configured to move inner shaft 16 between the retracted, extended and release configurations.

Handle assembly 40 may be coupled to inner shaft 16 via one or more suitable coupling methods, e.g., one or more suitable adhesives. Alternatively, handle assembly 40 may be formed monolithically with inner shaft 16. Handle assembly 40 includes a distal end 42 having an ergonomic configuration that facilitates grasping by a user. Specifically, distal end 42 includes two generally arcuate portions 44a, 44b that are configured for grasping by a user. Arcuate portions 44a, 44b are configured to accommodate fingers of the various contemplated users.

A proximal end 46 of handle assembly 40 is configured to releasably couple to a cinch puller 48. With this purpose in mind, proximal end 46 of handle assembly 40 includes a generally arcuate configuration that complements a generally arcuate configuration of cinch puller 48. A pair of relatively flexible finger portions 50a, 50b are provided at proximal end 46 and are configured to releasably couple to a pair of corresponding indents 52a, 52b that are provided on cinch puller 48 (as best seen in FIG. 2). Moreover, an indent/detent interface may be utilized to facilitate aligning cinch puller 46 with handle assembly 40. Specifically, a pair of detents 56a, 56b may be provided at proximal end 46 and configured to engage a pair of corresponding indents 58a, 58b that may be provided at a distal end 60 of cinch puller 48 (FIG. 4).

Cinch puller 48 is configured to close pouch 18 after a tissue specimen is positioned therein. To this end, a cinch (e.g., a suture "S," thread, wire, cable or the like) is threaded through an aperture 59 that extends through cinch puller 48. A knot "K" (FIG. 2) of suitable configuration (e.g., a knot sized not to fit through aperture 59) is provided at a distal end of suture "S" and is configured to connect suture "S" to cinch puller 48. As can be appreciated, other devices (e.g., a tab) may be utilized in place of knot "K" to connect suture "S" to the cinch puller 48. The distal end of suture "S" is feed through aperture 59 and is positioned within one or more grooves 55 defined through a side surface of handle assembly 40 and into a corresponding groove 38b on inner shaft 16 to couple to pouch 18 (FIG. 4). An optional cutting mechanism 51 that may be provided on handle assembly 40.

Specifically, cutting mechanism 51 (as best seen in FIG. 2) may be a part of handle assembly 40 and may be configured to sever suture "S" after tissue is positioned within pouch 18 and pouch 18 is closed. In the illustrated embodiment, for example, cutting mechanism 51 is in the form of cutting blades 53 that are seated within a recess (not explicitly shown) defined in handle assembly 40. Cutting blades 53 may include a "butterfly" configuration that allows cutting blades 53 to be installed in handle assembly 40 without the need for riveting or gluing. That is, cutting blades 53 may be press-fit within the recess. As can be appreciated, this may decrease the overall manufacturing cost of specimen retrieval device 10. A central aperture 57 of suitable configuration (e.g., having a diameter slightly smaller than a diameter of suture "S") is provided between cutting blades 53 and is configured to grasp a portion of suture "S" that is left coupled to pouch 18; this allows a clinician to maintain control of suture "S" including pouch 18 after pouch 18 is closed.

Continuing with reference to FIGS. 2-4, groove 38b and a groove 38c may be provided on inner shaft 16 and may extend along a length of inner shaft 16 to receive respective suture "S" and retention pin 30 therein. Grooves 38b, 38c maintain respective suture "S" and retention pin 30 in a relatively fixed orientation therein such that suture "S" and retention pin 30 do not hinder translation of inner shaft 16 with respect to outer shaft 14 when inner shaft 16 is moved to deploy and/or retract pouch 18. One or more bridges (not shown) may extend across grooves 38a-38c and may be utilized to maintain leaf spring 24, suture "S" and retention pin 30 in respective grooves 38a-38c. Moreover, one or more O-rings 39 (see FIGS. 6A-6B for example) are provided at a distal end 43 of inner shaft 16 are also configured to facilitate maintaining leaf spring 24, suture "S" and retention pin 30 in their respective grooves 38b, 38c. O-rings 39 seat within corresponding recesses (not explicitly shown) that are defined on an outer surface of inner shaft 16. O-rings 39 are also configured to provide adequate clearance between outer shaft 14 and inner shaft 16 so as to allow unhindered translation of inner shaft 16 with respect to outer shaft 14 when inner shaft 16 is translated in the proximal and/or distal directions. Moreover, O-rings 39 also provide a fluid tight seal to maintain insufflation gases in a working space, e.g., within a peritoneal cavity of a patient.

Referring now to FIGS. 5, 6A and 6B, retention pin 30 is configured to releasably couple to pouch 18 and engage flange 26 when leaf spring 24 is moved distally past stop pin 22. To these ends, retention pin 30 is configured to releasably couple to pouch 18 so as to allow a user to move pouch 18 and also so as to allow a user to selectively disconnect pouch 18 from the inner shaft 16. Specifically, a proximal coupling portion 35 of pouch 18 has an opening or aperture 35a through which the retention pin 30 is initially passed. The inner shaft 16 has near its distal end 43 a notch 433 which defines a proximal notch face 431 and a distal notch face 432. In its initial position, the retention pin 30 extends fully between the notch faces such that the pouch 18 is attached to the distal end 43 of the inner shaft 16 and will not inadvertently become disengaged therefrom.

Retention pin 30 has at its proximal end a radially-extending tip 36 (FIGS. 2 and 5) that is configured to engage flange 26. Specifically, tip 36 engages flange 26 when leaf spring 24 disengages from stop pin 22 and inner shaft 16 is moved a predetermined distance "D" distally, as best seen in FIG. 2. In accordance with the instant disclosure, with tip 36 engaged with flange 26 and inner shaft 16 moved distally a distance "D," the retention pin 30 is moved proximally relative to the inner shaft 16 such that the distal most end of the retention pin 30 becomes spaced apart from the distal notch face 432. As a result of this retraction of the retention pin 30, the pouch 18 can be uncoupled from retention pin 30, e.g., proximal movement of inner shaft 16 causes pouch 18 to uncouple from a pair of resilient fork members 64, 66 of pouch support mechanism, e.g., a spring 62.

Referring to FIGS. 6A-6B, spring 62 operably couples to a distal end 43 of inner shaft 16 via one or more suitable coupling methods and includes two flexible or resilient members 64 and 66 that form an open fork configuration (FIGS. 1 and 6A-6B). In the illustrated embodiment, inner shaft 16 at distal end 43 thereof is overmolded to a proximal end 68 of spring 62. Other coupling methods may also be utilized to couple spring 62 to distal end 43. For example, one or more pins, rivets or the like may be utilized to couple proximal end 68 to distal end 43.

Resilient members 64, 66 are configured to move from a stressed or non-expanded state (e.g., when pouch 18 is in a retracted configuration, see FIG. 9 for example) to an unstressed or expanded state (e.g., when pouch 18 is deployed from outer shaft 14 (see, e.g., FIGS. 1, 6A-6B and 8). In the unstressed or expanded condition, resilient members 64, 66 collectively form a generally U-shaped configuration for supporting a periphery of an opening 15 of pouch 18, see FIG. 7A for example.

Figure 8:
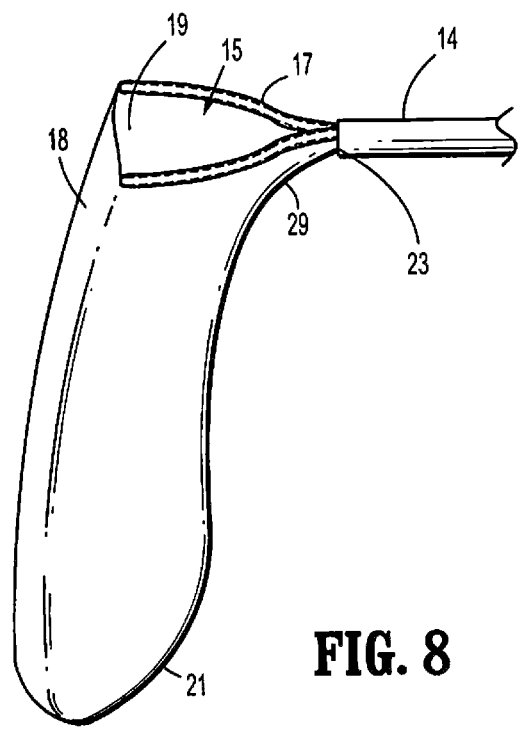
FIG. 8 is a perspective view of the short pouch depicted in FIG. 7A in a "normal use" configuration.

In accordance with the instant disclosure, resilient members 64, 66 are configured to releasably couple to pouch 18. Specifically, resilient members 64, 66 are feed through a tubular portion or sleeve 17 of suitable configuration that is provided on pouch 18 (FIG. 8). Accordingly, subsequent to pouch 18 being uncoupled from retention pin 30, proximal movement of inner shaft 16 within outer shaft 14 causes a portion of pouch 18, e.g., sleeve 17, to contact a distal end of outer shaft 14, which, in turn, results in resilient members 64, 66 sliding out from sleeve 17 and pouch 18 uncoupling from resilient members 64, 66.

Referring to FIGS. 7A-8, pouch 18 may be made from any suitable biocompatible materials (e.g., nylon) capable of forming an impermeable flexible membrane. Pouch 18 includes a generally tubular or elongated configuration that is defined by an openable and closable upper portion or mouth 19 and closed lower portion 21. Upper portion 19 includes circumferential sleeve 17 that is configured to receive resilient members 64, 66 therein and a distal end of suture "S." Sleeve 17 may be formed on pouch 18 via any suitable forming methods. In embodiments, for example, a top portion of pouch 18 may be folded into an interior thereof and, subsequently, glued thereto. As noted above, suture "S" is configured to close pouch 18 when cinch puller 48 is pulled proximally. Thus, unlike resilient members 64, 66 which are releasably coupled to pouch 18, suture "S" is intended to remain connected to pouch 18 by virtue of the fact that the suture is looped through the slot/sleeve 17 of the pouch.

Unlike conventional pouches that typically include a proximal edge having a profile that is generally straight and perpendicular to the longitudinal axis A, pouch 18 may, in various embodiments, include a proximal edge 23 that has a curved profile 29. For example, in an embodiment, the proximal edge of the pouch 18 is initially at a very obtuse angle, nearly 180 degrees, relative to the longitudinal axis at or near the mouth of the pouch 18. The proximal edge of the pouch 18 gradually becomes closer to being orthogonal relative to the longitudinal axis near to the bottom of the pouch 18. This curvature profile at the proximal edge of the pouch 18 may have any such curvature, but in an embodiment, may define a concave curvature at or near the mouth of the pouch 18 and may further define a convex curvature at or near the bottom portion 21 of the pouch 18. The above-described features may facilitate retraction of pouch 18 within outer shaft 14 by reducing the force required to be exerted by a user in order to move inner shaft 16 proximally relative to the outer shaft 14. Moreover, unlike conventional specimen retrieval devices that are typically shipped for use with a pouch that is folded or rolled and stored within the outer shaft, specimen retrieval device 10 may be shipped for use with pouch 18 in an unfolded and deployed configuration. As can be appreciated, a pouch that is folded or rolled and stored within the outer shaft during shipping may result in undesirable memory wrinkles being formed thereon, which, in turn, may make it difficult for a clinician to open the pouch when it is deployed from the applicator. Such a disadvantage may be avoided by an arrangement as described herein.

The pouch 18 may have any of a variety of different configurations. FIG. 12 is a perspective view of a specimen retrieval device in accordance with an embodiment of the present disclosure with a pouch in a deployed configuration. In this configuration, the pouch 18 has an hourglass shape. Specifically, the pouch 18, in this embodiment, has a region having a waist "W". The waist may have a dimension in the radial direction, e.g., a direction that is in a plane generally parallel to the plane defined by the patient's tissue wall being traversed, that is less than the dimension of the mouth of the pouch 18. In this way, when the pouch is deployed into an incision, the waist of the pouch 18 may be arranged within the laparotomy site, while the portions of the pouch 18 that are above the waist may remain outside of the incision. Likewise, when the pouch is deployed into an incision and the waist of the pouch 18 is arranged within the laparotomy site, the portions of the pouch 18 that are below the waist may remain fully inside of the surgical space, e.g., below the incision. Such an arrangement may allow for easier morcellation. Furthermore, such an arrangement may allow for easier access to the contents of the pouch 18 after the inner shaft and the pouch support mechanism has been removed. For example, when the pouch support mechanism has been removed from a conventional specimen retrieval product, the mouth of the pouch 18 is positioned within the surgical space, making it difficult for a user to access the mouth, e.g., for the purposes of inserting a morcellation instrument or the like. In contrast, the arrangement shown in FIG. 12 permits a user to readily access the mouth of the pouch 18 even when the pouch support mechanism has been detached from the pouch 18 and removed therefrom, because the mouth of the pouch 18 is positioned outside of the surgical space.

Figure 13A:
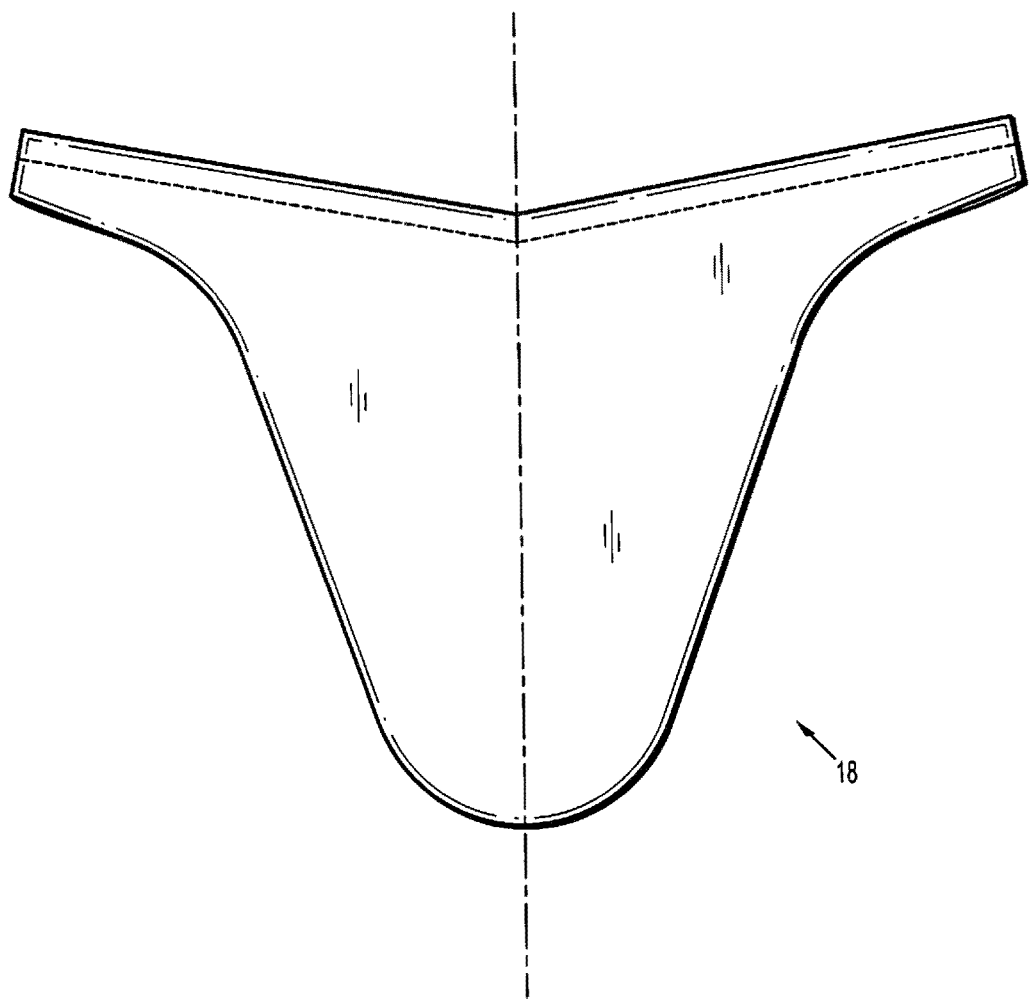
FIGS. 13A-C are top views of a pouch for a specimen retrieval device in accordance with another embodiment of the present disclosure, with the pouch in a pre-fabricated state.
Figure 13B:
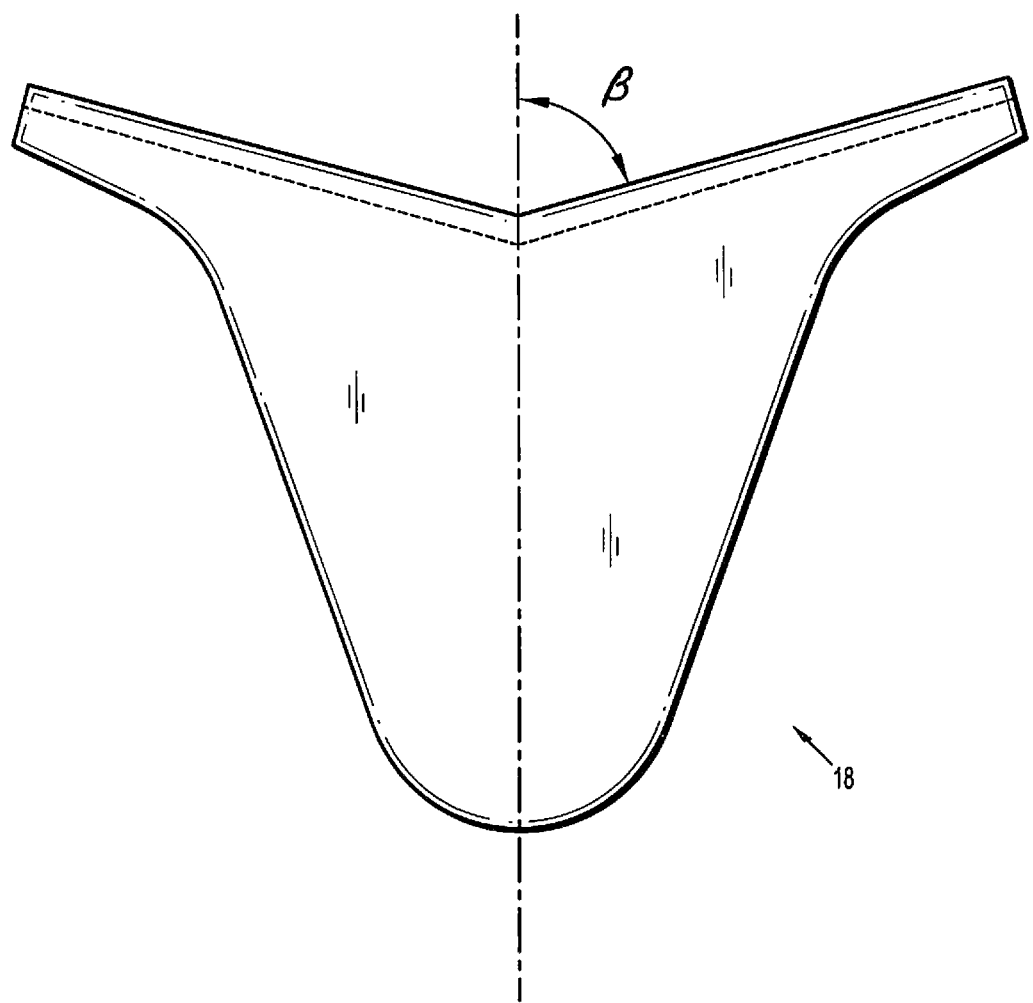
Figure 13C:
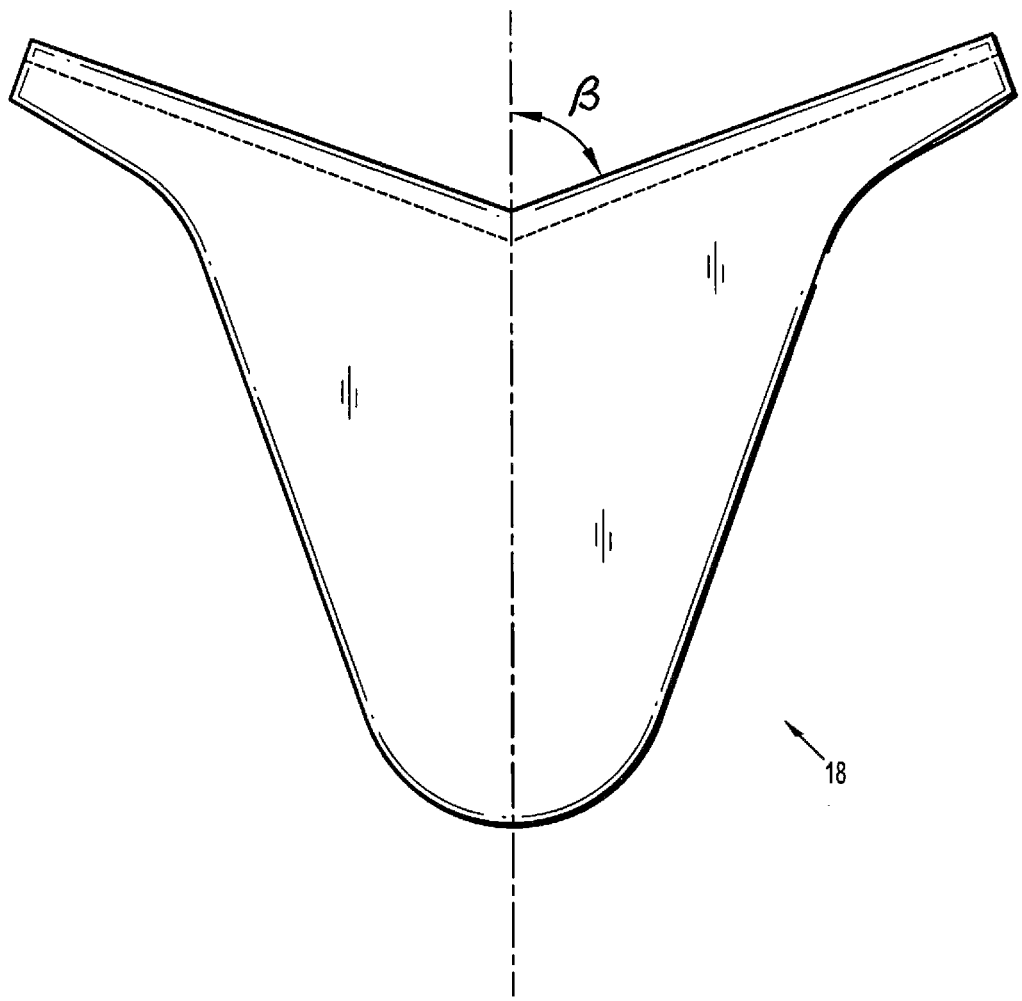
Figure 13D:
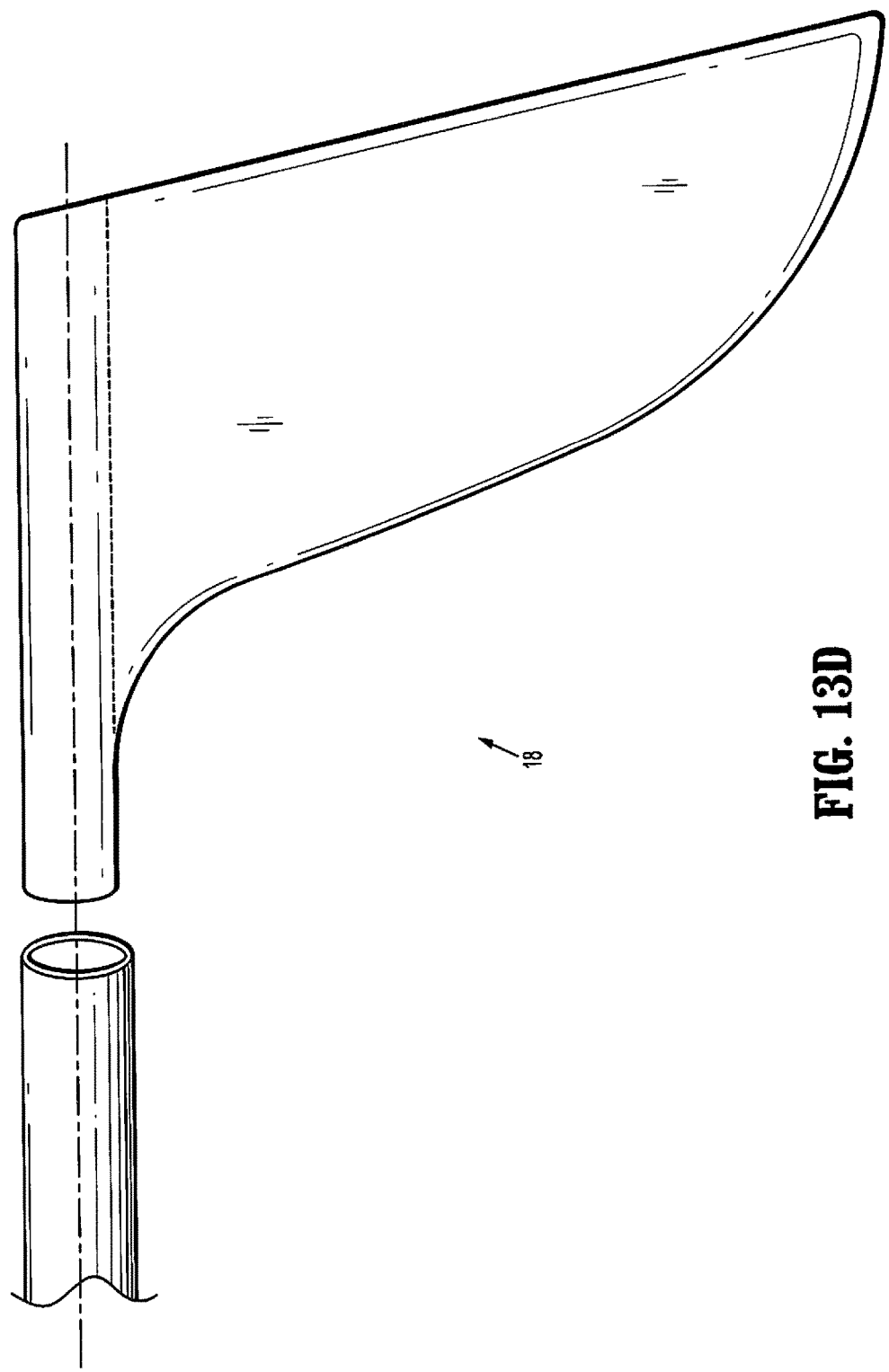
FIG. 13D is a side view of a pouch for a specimen retrieval device in accordance with the embodiment shown in FIGS. 13A-C, with the pouch in a fabricated state.

The pouch 18 may be fabricated in various different manners. Advantageously, the pouch 18 is made from a single piece of material, e.g., rip-stop nylon, polyurethane, etc., that, prior to fabrication, is in the form of a flat sheet. FIGS. 13A-C are top views of a pouch for a specimen retrieval device in accordance with another embodiment of the present disclosure, with the pouch in a pre-fabricated state. The pouch 18 is shown as being symmetrical about a vertical (in this view) midline. This vertical midline will be the location of a fold. The upper portion of the pouch 18 (in this view) provides the mouth of the pouch 18, and is advantageously folded over and welded in place so as to form a slot around the mouth of the pouch 18. Of course, joining methods other than welding may also be employed, e.g., gluing, mechanically fastening, etc. In this embodiment, this upper portion tapers towards the vertical midline at a single angle. The right and left sides of the pouch (in this view) form a complex curve that, as described in further detail hereinabove, provides a curved proximal edge that is more easily pulled by the inner shaft into the outer shaft during use. In an embodiment, the right and left sides of the pouch 18 are brought together during fabrication by the pouch 18 being folded about the vertical midline, with the right and left sides of the pouch being welded or otherwise joined together in a sealing manner. This folding method of fabrication reduces the linear length of welding that needs to occur in order to provide a pouch that is fully sealed around its edges (except for the mouth). FIGS. 13A, B, and C are similar to each other and differ from each other only in the angles 13 formed by the edges. FIG. 13D is a side view of a pouch for a specimen retrieval device in accordance with the embodiment shown in FIGS. 13A and C, with the pouch in a fabricated state, illustrating the bag fold line and the complex curve provided by the weld on the proximal sides.

Figure 14A:
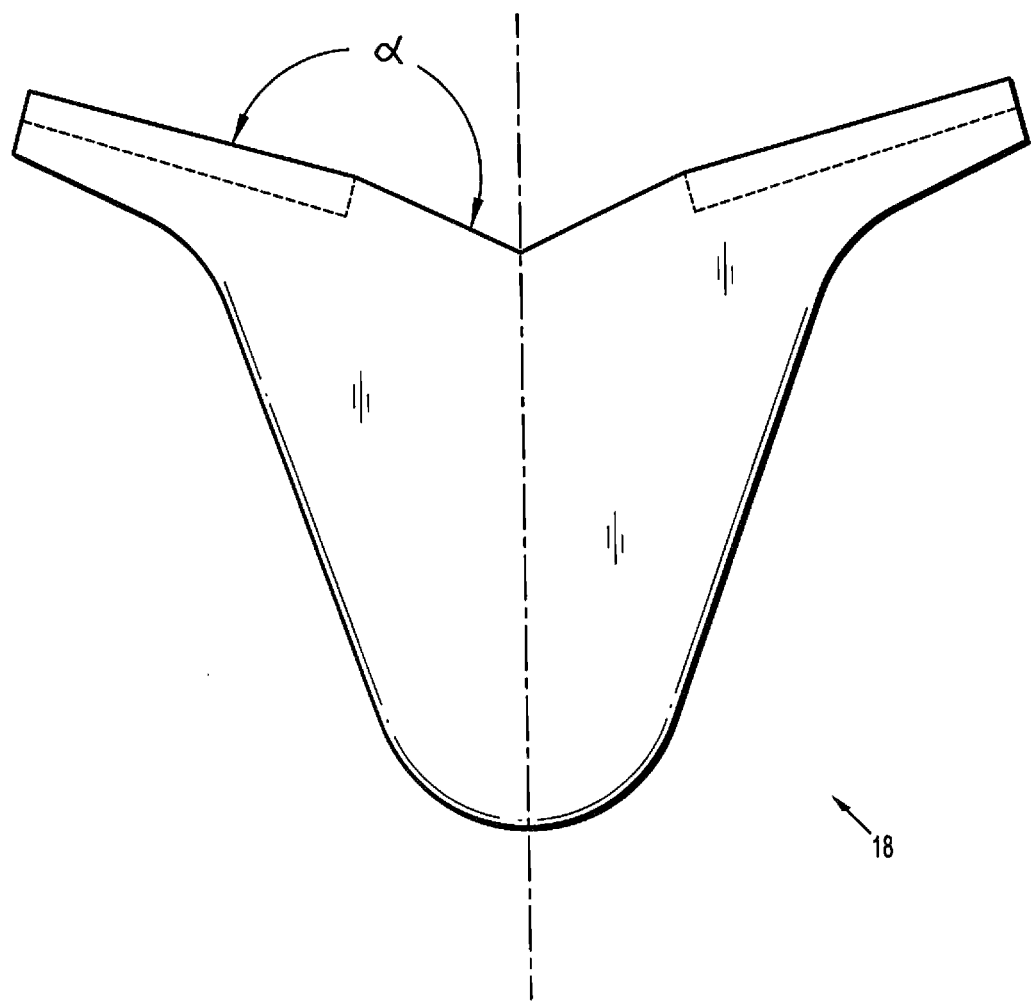
FIG. 14A is a top view of a pouch for a specimen retrieval device in accordance with another embodiment of the present disclosure, with the pouch in a pre-fabricated state.
Figure 14B:
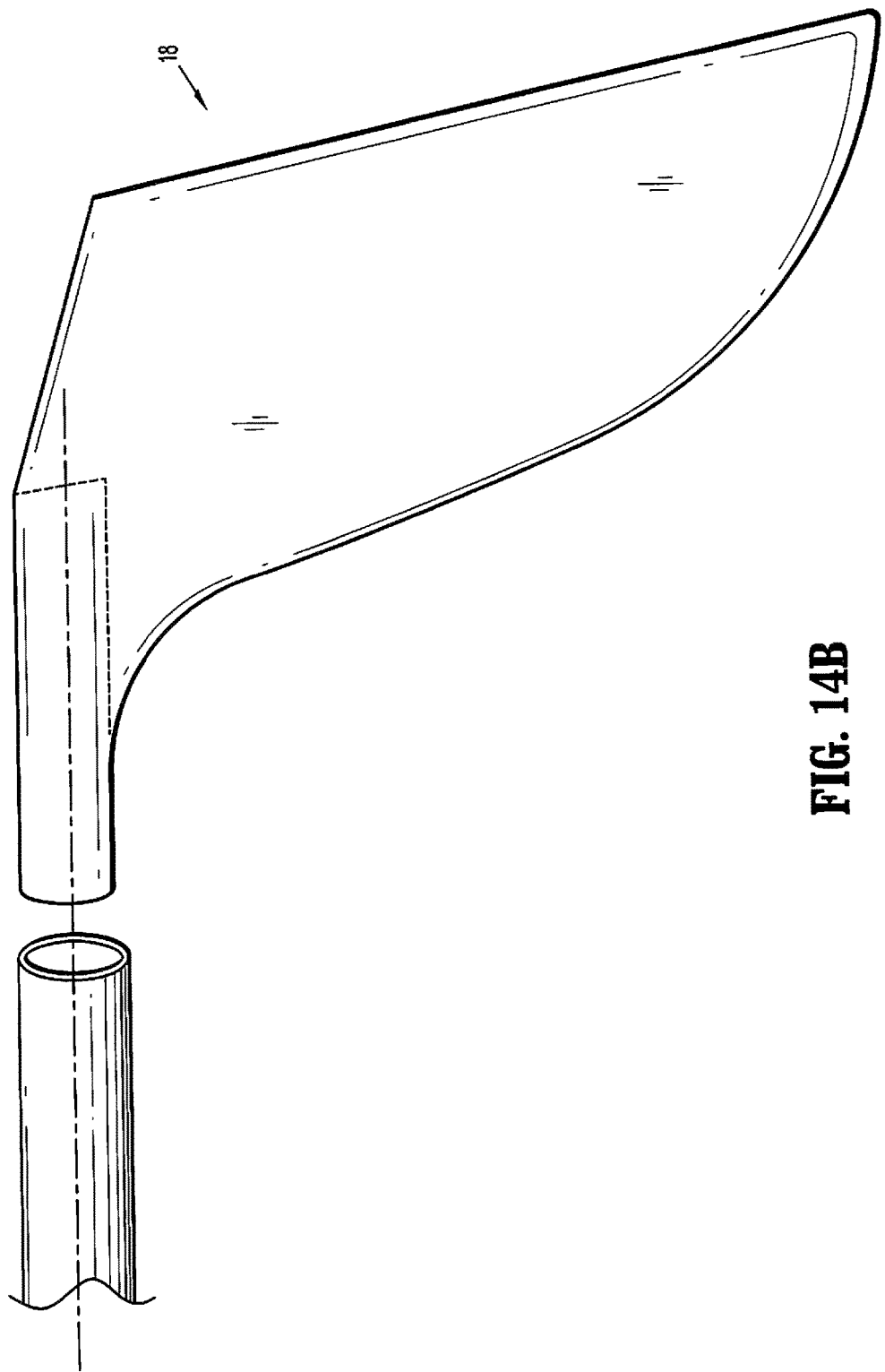
FIG. 14B is a side view of a pouch for a specimen retrieval device in accordance with the embodiment shown in FIG. 14A, with the pouch in a fabricated state.

As mentioned previously, FIG. 14A is a top view of a pouch for a specimen retrieval device in accordance with another embodiment of the present disclosure, with the pouch in a pre-fabricated state. Similar to the embodiment shown in FIGS. 13A-D, the pouch 18 of FIGS. 14A and B are shown as being symmetrical about a vertical (in this view) midline. This vertical midline provides the location of a fold. The right and left sides of the pouch (in this view) form a complex curve that, as described in further detail hereinabove, provides a curved proximal edge that is more easily pulled by the inner shaft into the outer shaft during use. Like the embodiment of FIGS. 13A-D, the right and left sides of the pouch 18 are brought together during fabrication by the pouch 18 being folded about the vertical midline, with the right and left sides of the pouch 18 being welded or otherwise joined together in a sealing manner. Again, this folding method of fabrication reduces the linear length of welding that needs to occur in order to provide a pouch that is fully sealed around its edges (except for the mouth), thereby reducing manufacturing complexity and lowering the cost of manufacturing the pouch. The pouch 18 of FIGS. 14A and B differs from the embodiments shown in FIGS. 13A-D in that each side of the upper portion of the pouch 18 (in this view) that provides the mouth of the pouch 18 forms a compound angle α. Each side of the mouth is advantageously folded over and welded in place so as to form a slot around the mouth of the pouch 18. The significance of this compound angle along the upper portion is illustrated in FIG. 14B, which is a side view of a pouch for a specimen retrieval device in accordance with the embodiment shown in FIG. 14A, with the pouch in a fabricated state. As shown in FIG. 14B, the increased angle provides for an opening in the pouch that more easily accepts a specimen. More specifically, during a surgical procedure in which the pouch 18 is positioned by a user to receive a specimen, the mouth of the pouch 18 is presented to a user at an angle that is more conducive to receiving the specimen.

In use, handle assembly 40 may be moved proximally to move inner shaft 16 including pouch 18 to a retracted configuration. Thereafter, outer shaft 14 may be inserted through a natural or man made orifice on a patient and positioned adjacent target tissue. Subsequently, handle assembly 40 may be moved distally to move inner shaft 16 including pouch 18 to a "normal use" configuration, e.g., leaf spring 24 is in contact with stop pin 22.

In the "normal use" configuration, target tissue may be dissected and positioned within pouch 18. A user may selectively and repeatedly move between the normal use and retracted configurations so as to collect various different tissue portions at different times during a surgical procedure, while temporarily pulling the entire mouth of the pouch 18 (along with the pouch support mechanism) into the distal end of the outer shaft 14 between such different times so as to ensure that the contents of the pouch are not spilled between such fillings. When a user is satisfied that all of the tissue to be collected has been placed within pouch 18, a user may depress push-button 34 to disengage leaf spring 24 from stop pin 22 and move handle assembly 40 distally, e.g., a distance "D." As a result thereof, tip 36 engages flange 26, which, in turn, causes retention pin 30 to move proximally relative to the inner shaft 16, thereby enabling the decoupling of pouch 18 from the inner shaft 16.

Once the pouch 18 has been de-coupled from the inner shaft 16, a user may detach the cinch puller 48 from the handle portion of the inner shaft and use the cinch cutter 53 to cut the suture "S." The entire inner shaft 16 may then be withdrawn out of the outer shaft 14, taking with it the pouch retention mechanism 30, the leaf spring 24, the pouch support mechanism of the resilient forks (which retract out of the slot 17 at the mouth of the pouch, etc. With the inner shaft 16 completely removed, the remaining portion of the cinch extends longitudinally through the outer shaft 14. By pulling the suture "S," the mouth of the pouch 18 is caused to close. The outer shaft 14 may then also be withdrawn from out of the surgical site, leaving just the closed pouch 18 within the surgical site and a portion of the suture "S" extending through the incision.

Figure 15A:
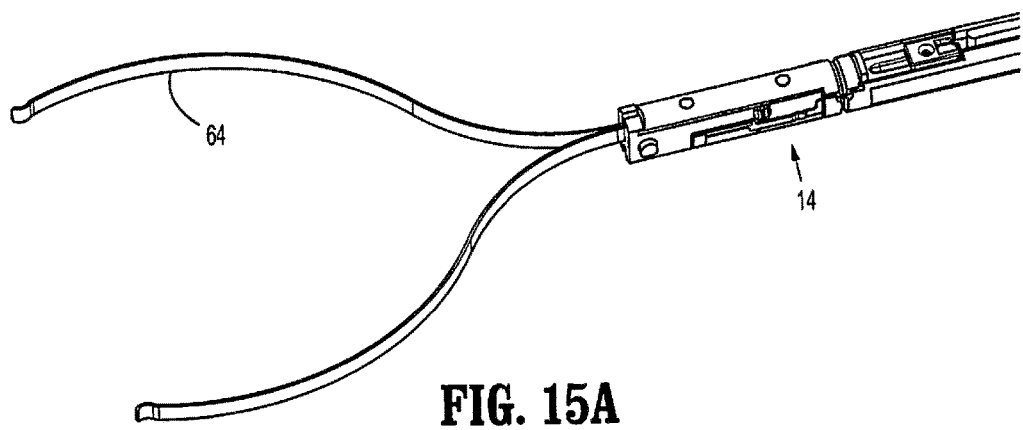
FIGS. 15A-D are top and bottom perspective views of a distal end of an inner shaft of a specimen retrieval device, in accordance with an embodiment of the present disclosure.
Figure 15B:
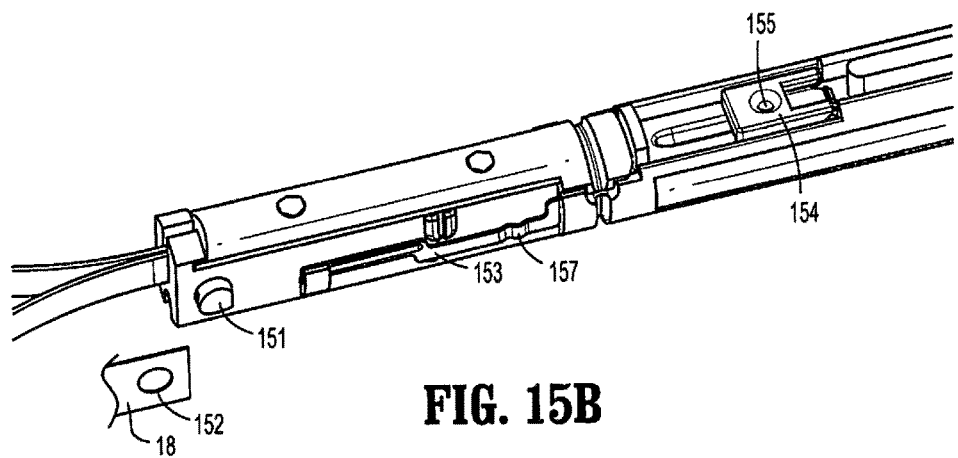
Figure 15C:
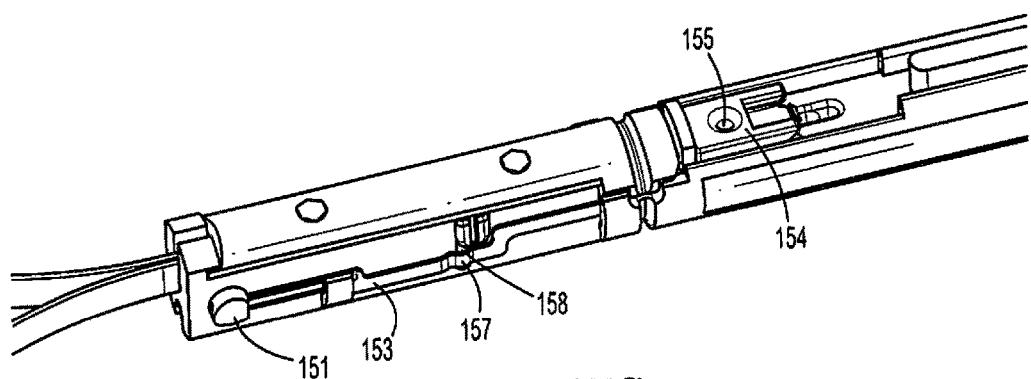
Figure 16A:
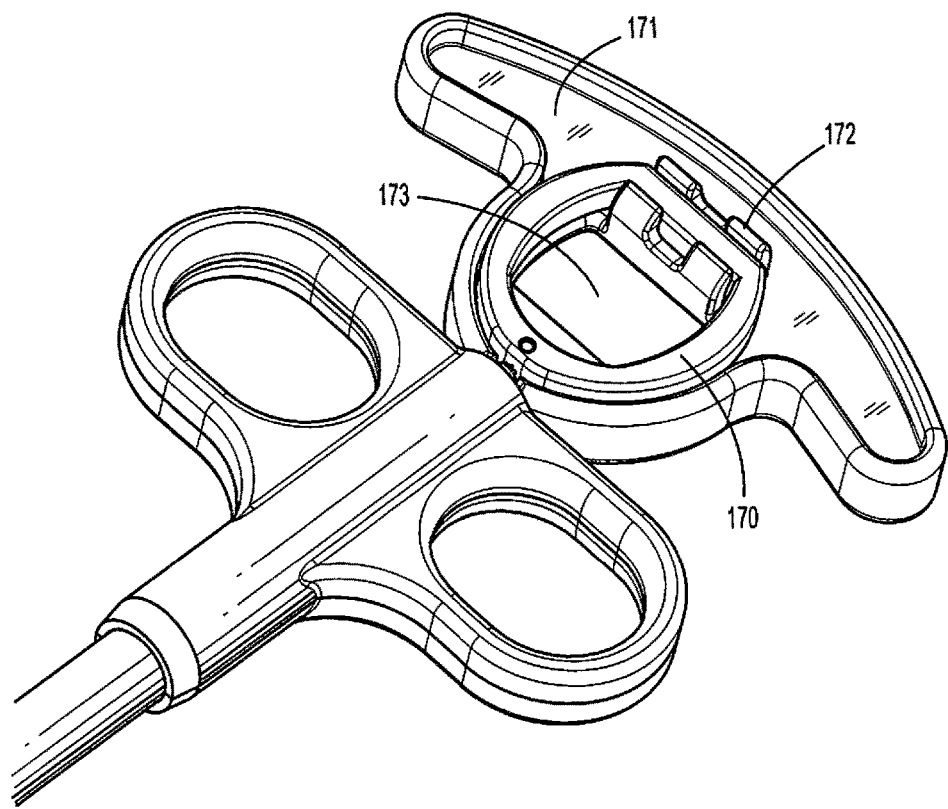
FIGS. 16A-B are perspective views of a proximal portion of a specimen retrieval device, in accordance with an embodiment of the present disclosure.
Figure 16B:
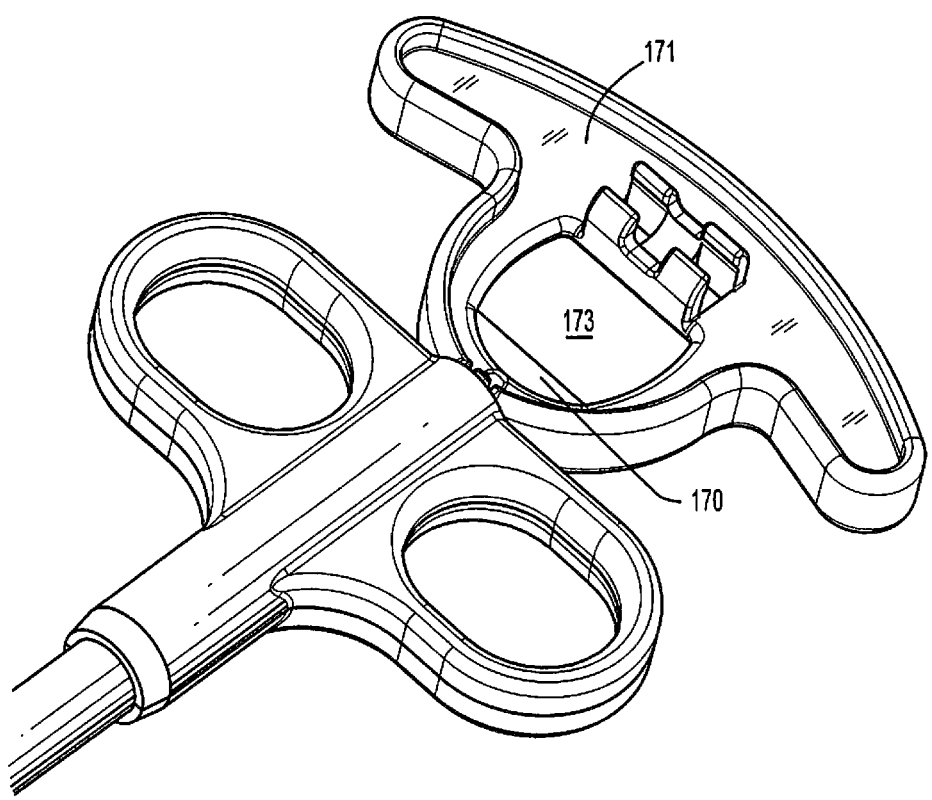
Figure 16C:
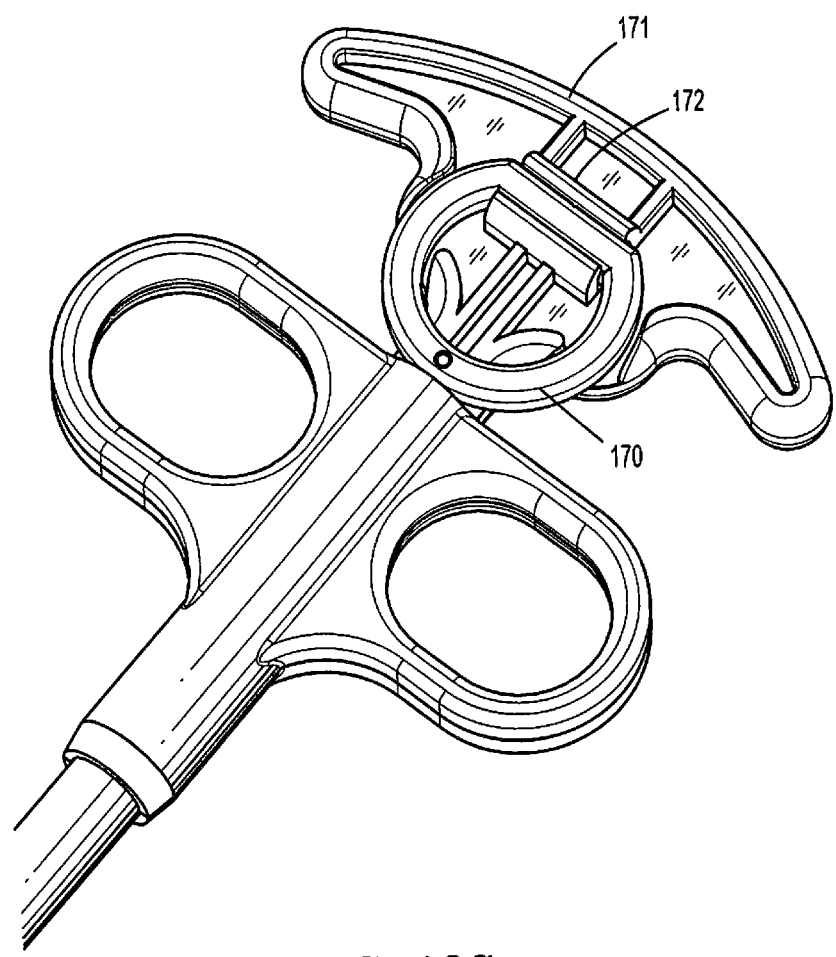
FIG. 16C is a perspective view of a proximal portion of a specimen retrieval device, in accordance with an embodiment of the present disclosure.

As set forth above, in an embodiments, one or more stop mechanisms may be employed to facilitate detachment of the pouch 18 from the pouch support mechanism at the distal end of the inner shaft 16. In other embodiments, the stop mechanisms may be eliminated and a different type of mechanism may be employed to facilitate detachment of the pouch 18 from the pouch support mechanism at the distal end of the inner shaft 16. FIGS. 15A-C illustrate several views of an embodiment which replace the retention pin 30 with a pair of sliding retention fingers 153. FIGS. 16A-C, on the other hand, illustrate several views of embodiments which replace the stop mechanisms with a movable member, e.g., a pivotable ring, which functions as an actuator for selectively moving the pair of sliding retention fingers 153.

Turning first to FIGS. 15A-D, there is provided an arrangement for a pouch retention mechanism that facilitates selective detachment of the pouch 18 from the pouch support mechanism at the distal end of the inner shaft 16. An advantage of the pouch retention mechanism described herein below may be the ease with which the pouch retention mechanism facilitates selective detachment of the pouch 18 from the pouch support mechanism. Conventional pouch retention mechanisms that enable detachment of the pouch 18 from the pouch support mechanism typically do so only when the pouch retention mechanism has been moved distally to a location that is distal relative to the distal end of the outer shaft. In order to prevent inadvertent detachment of the pouch from the pouch support mechanism, conventional pouch retention mechanisms may rely on various stop mechanisms to prevent the pouch retention mechanism from being moved distally to a location that is distal relative to the distal end of the outer shaft.

In various embodiments, the arrangement described hereinbelow may eliminate the need for such stop mechanisms. For example, as described in further detail below, the arrangement of the presently described devices may include a pouch retention mechanism that permits selective detachment of the pouch from the pouch support mechanism while the pouch retention mechanism is still within the outer shaft 16. By eliminating the conventional stop mechanisms, the device may be simplified and require fewer steps to be performed by a user during a surgical procedure. In addition, the cost of the device may be reduced as a result of there being fewer components, thereby decreasing component costs and simplifying manufacture.

As in the previously described embodiments, the pouch 18 has holes 152 defined by the pouch material and being adjacent to the proximal end of the mouth. Instead of these holes 152 having a single retention pin 30 positioned through them, each one of the holes 152 in this embodiment has positioned therethrough a protrusion 151 of the inner shaft 16. Each one of these protrusions 151 protrudes laterally from an outer surface of the inner shaft 16. Each one of the protrusions 151 is engaged by a respective one of a pair of sliding retention fingers 153 that slide longitudinally relative to the inner shaft 16, e.g., along an outside surface of the inner shaft 16. It should be recognized that, in other embodiments, the retention fingers 153 may move in various different ways, not merely by sliding, e.g., by pivoting, rotating, etc. It should also be recognized that, while these members are described herein as being elongated finger-type structures, other structures may also be employed.

When each one of the pair of sliding retention fingers 153 is in a distal most position relative to the inner shaft 16, the distal end of the sliding retention finger 153 abuts the protrusion 151 such that the hole 152 of the pouch that is positioned through the protrusion 151 is prevented from being disengaged from, e.g., slipping off of, the protrusion 151. When the sliding retention finger 153 is actuated in a proximal direction relative to the inner shaft 16 by a user, the sliding retention fingers 153 no longer abut the protrusions 151. A separating force that is exerted on the inner shaft 16 relative to the pouch 18 at this point enables the hole 152 to be disengaged from the protrusion 151 and thus enables the pouch 18 to be detached from the pouch support mechanism at the distal end of the inner shaft 16.

Such a separating force may be generated by a user pulling proximally on the handle at the proximal end of the inner shaft 16. For example, once the hole 152 of the pouch 18 is no longer locked onto the protrusion 151 by the sliding retention finger 153, pulling the inner shaft 16 proximally does not pull the pouch 18 and pouch support mechanism back into the outer shaft 14 (as it did when the hole 152 of the pouch 18 was locked onto the protrusion 151 by the sliding retention finger 153), but rather the pouch support mechanism is caused to slide out of the slots around the mouth of the pouch 18, until the pouch support mechanism is no longer supporting the pouch 18. This disengagement of the pouch 18 from the pouch support mechanism occurs because the friction experienced between the pouch 18 and the outer shaft 14 by the unfolded pouch 18 attempting to be pulled into the small cross-sectional area of the outer shaft 14 is greater than the frictional force that holds the pouch support mechanism in the slots around the mouth of the pouch 18.

In the embodiment shown, the sliding retention fingers 153 are attached to a cinch, e.g., suture, attachment mechanism 154. The sliding retention fingers 153 may be separate components from the cinch, e.g., suture, attachment mechanism 154 and may be attached thereto by any suitable method, e.g., overmolding, friction fit, snap-lock fitting, welding, etc. Alternatively, the sliding retention fingers 153 may be integrally formed with the cinch, e.g., suture, attachment mechanism 154. As shown, the cinch, e.g., suture, attachment mechanism 154 defines an opening 155 through with the cinch, e.g., suture, 156 may be positioned and secured. A force exerted on the cinch, e.g., suture, 156, e.g., by a user actuating an actuator (described in further detail below), exerts a force on the cinch, e.g., suture, attachment mechanism 154 which, in turn, exerts a force on the sliding retention fingers 153 to move the sliding retention fingers 153 proximally relative to the inner shaft 16.

In an embodiment, the inner shaft 16 and the sliding retention fingers 153 may have corresponding features that prevent the sliding retention fingers 153 from inadvertently moving proximally relative to the inner shaft 16. As shown, the sliding retention fingers have an indent 157 and the inner shaft 16 has corresponding detents 158 that are frictionally engaged thereby. The force required to be exerted on the sliding retention fingers 153 to move the sliding retention fingers 153 proximally relative to the inner shaft 16 should be higher than the frictional force between the indent 157 of the sliding retention fingers 153 and the corresponding detents 158 of the inner shaft 16.

Of course, it should be recognized that, while the embodiment shown and described hereinabove employs an arrangement in which the pouch 18 has two holes 152, two protrusions 151 and two sliding retention fingers 153, other embodiments may employ a different number of these components, e.g., either one or more than two. For example, in accordance with an embodiment, an arrangement may be provided whereby the pouch 18 has only one hole 152, the inner shaft 16 having only a single protrusion 151 which is positioned through the hole 152, the protrusion 151 being engaged by a single sliding retention finger 153. In such an embodiment, the pouch 18 is maintained on the distal end of the inner shaft 16 by protrusion 151 protruding through the hole 152 and by the sliding retention finger 153 engaging the protrusion such that the hole 152 is prevented from being disengaged by the protrusion 151.

The pouch 18 is selectively detached from the distal end of the inner shaft 16 by the actuation of the sliding retention finger 153 in a proximal direction relative to the inner shaft 16, thereby permitting the hole 152 to be disengaged from the protrusion 151. Still further, it should be recognized that these components need not be equal in number, e.g., a single protrusion 151 may be positioned through a plurality of holes 152, a single sliding retention finger 153 may engage a plurality of protrusions 151 and/or holes 152, a plurality of sliding retention fingers 153 may engage a single protrusion 151 and/or hole 152, etc.

Figure 15D:
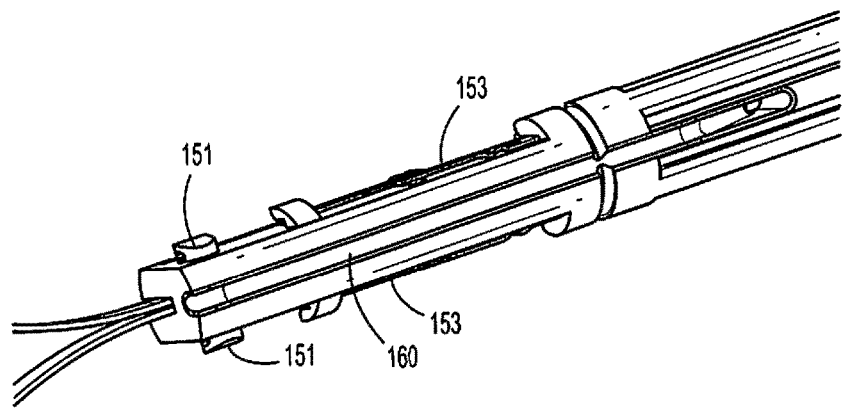

FIG. 15D illustrates a bottom perspective view of the distal end of the inner shaft 16. An underside of the inner shaft 16 shows a track 160 for the cinch, e.g., suture, 156. The cinch, e.g., suture, 156 resides within the track 160 and extends from the pouch 18, along the underside of the inner shaft 16, then up and through the middle of the inner shaft 16, then through the opening 155 in the cinch, e.g., suture, attachment mechanism 154 and then it continues proximally along the top of the inner shaft 16.

As set forth above, FIGS. 16A-C illustrate several views of embodiments which replace the stop mechanisms with a movable member, e.g., a pivotable ring, which functions as an actuator for selectively moving the pair of sliding retention fingers 153. For example, FIGS. 16A-B illustrate several views of an embodiment which employ a movable member, e.g., a pivotable ring, which is connected to a proximal end of the cinch, e.g., suture, 156 and that functions as an actuator for selectively moving the pair of sliding retention fingers 153. FIG. 16C, on the other hand, illustrates an embodiment which employs a pivotable ring that is connected to a proximal end of the cinch, e.g., suture, 156 and that functions for the same purpose.

Referring to FIGS. 16A and B, there is provided an actuator for selectively moving the pair of sliding retention fingers 153. In this embodiment, the actuator is a pivotable ring 170. The pivotable ring 170 is pivotably attached at its proximal end to a handle 171. In an embodiment, the proximal end of the pivotable ring 170 is snap-fit into a groove 172 on the handle 171. The handle 171 is attached to the proximal end of the inner shaft 16 and is configured to be gripped by a user for moving the inner shaft 16 longitudinally relative to the outer shaft 14. The distal end of the pivotable ring 170 is connected to the cinch, e.g., suture, 156.

When a user determines that he or she has placed all of the tissue that is desired to be placed in the pouch 18, the user may pivot the distal end of the ring 170 by lifting it up and pivoting it relative to the handle 171. This pivoting movement pulls on the cinch, e.g., suture, 156 so as to actuate the sliding retention fingers 153 and thereby permit the detachment of the pouch 18 from the pouch support mechanism, as described previously. With the pouch 18 detached from the pouch support mechanism, e.g., with the resilient forks 64 and 66 withdrawn from out of the slots around the mouth of the pouch 18, the cinch, e.g., suture, 156 may be cut, which allows the inner shaft 16 to be retracted from out of the outer shaft 14. With the inner shaft 16 retracted from out of the outer shaft 14, a user may pull on the proximal end of the cinch, e.g., suture, 156 in order to cinch the mouth of the pouch 18 closed. The outer shaft 14 may then be withdrawn from out of the incision, leaving just the cinch, e.g., suture, 156 passing through the incision with the pouch 18 inside of the incision. The contents of the pouch 18 may be morcellated, if desired (either through the outer shaft 14 prior to the outer shaft 14 being withdrawn, or through the incision if the outer shaft 14 has already been withdrawn), and the pouch 18 may then be withdrawn through the incision.

In the embodiment shown in FIGS. 16A and B, the ring 170 overlaps with the handle 171 except for a region of the ring 170 that is radially within a void 173 of the handle 171. Thus, in order to cause the ring 170 to pivot relative to the handle 171, a user reaches through the void 173 and presses upwardly against the ring 170 so as to pivot it relative to the handle 171. In the embodiment shown in FIG. 16C, the ring 170 overlaps with the handle 171 except for a region of the ring 170 that is proximal to the handle 171. Thus, in order to cause the ring 170 to pivot relative to the handle 171, a user places his or her fingers on the proximal end of the handle and presses upwardly against the ring 170 so as to pivot it relative to the handle 171. The embodiment shown in FIGS. 16A and B may be advantageous in that there may be less likelihood that a user will inadvertently pivot the ring 170 relative to the handle 171 since the user needs to place his or her fingers in a region of the handle 171, e.g., through the void 173 defined by the handle 171, which is different from the region of the handle 171 that his or her fingers are already in to move the handle 171 and the inner shaft 16 proximally and distally relative to the outer shaft 14.

The ability of the specimen retrieval device 10 to be repeatedly moved into and out of the distal end of the outer shaft 14 enables the device to be shipped with pouch 18 in an unfolded and deployed configuration, e.g., outside of the outer shaft 14. Such an arrangement may overcome an aforementioned drawback typically associated with conventional specimen retrieval devices, e.g., the likelihood of memory wrinkles being formed on pouch 18 is reduced, if not eliminated.

From the foregoing and with reference to the various figure drawings, those skilled in the art will appreciate that certain modifications can also be made to the present disclosure without departing from the scope of the same. For example, one or more devices or components may be utilized to indicate to a user when forks 64 and 66 are completely within the outer shaft 14. Such an indication may be useful so that a user will know that the mouth of the pouch 18, which is being supported by the forks 64 and 66, is also captured within the outer shaft 14, ensuring that the contents of the pouch 18 will not inadvertently spill out of the mouth of the pouch 18.

Specifically, with reference to FIGS. 10 and 11 a specimen retrieval device 110 according to an alternate embodiment of the present disclosure is illustrated. Specimen retrieval device 110 is similar to specimen retrieval device 10. Accordingly, only those features unique to specimen retrieval device 110 are described herein.

An inner shaft 116 includes one or more indication mechanisms 180 thereon that are configured to indicate to a user when forks 64 and 66 are positioned within an outer shaft 114. In an embodiment, indication mechanism(s) 180 may be in the form of indicia that are visible to a user when forks 64 and 66 are fully within the outer shaft 14. In one particular embodiment, for example, indicia may include one or more markings "M" on inner shaft 116 that are visible to a user when forks 64 and 66 are fully within the outer shaft 14. When the forks 64 and 66 are not fully within the outer shaft 14, the indicia may be hidden by the housing.

Alternatively, indication mechanism(s) 180 may be a structure that provides an audible sound perceivable to a user when forks 64 and 66 are fully within the outer shaft 14 (FIG. 11). In this particular embodiment, one or more components may be provided on inner shaft 116 and/or outer shaft 114 and may be configured to provide an audible "click" that is perceivable to a user to indicate when forks 64 and 66 are fully within the outer shaft 14.

Alternatively, indication mechanism(s) 180 may be a tactile feature "T" that is perceivable to user when forks 64 and 66 are fully within the outer shaft 14 (FIG. 11). In this particular embodiment, one or more components, e.g., an indent/detent configuration, may be provided on inner shaft 116 and/or outer shaft 114 and may be configured to provide an tactile "feel" that is perceivable to a user when forks 64 and 66 are fully within the outer shaft 14.

Figure 17A:
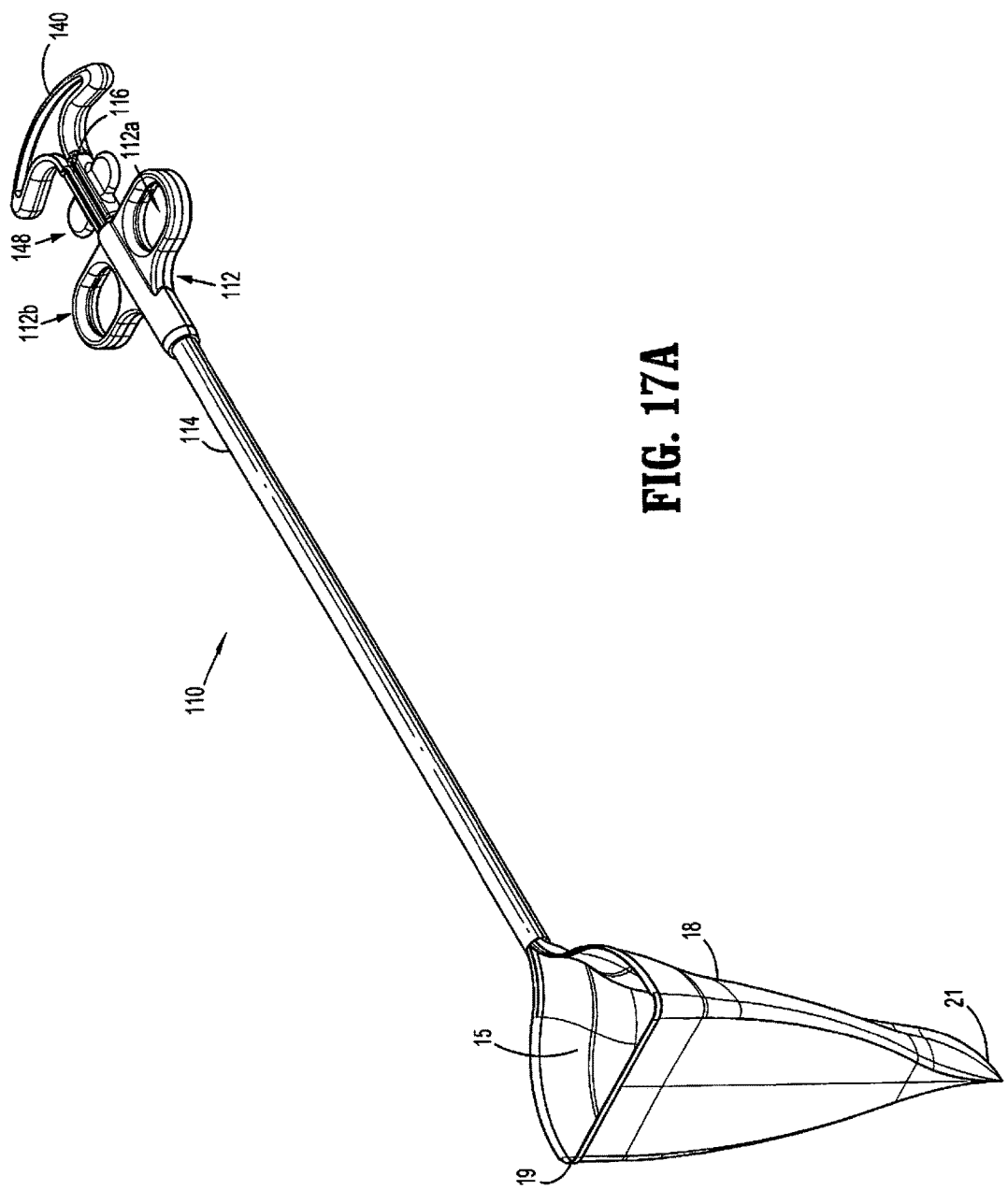
FIGS. 17A-17B are perspective views of a specimen retrieval device in accordance with another embodiment of the present disclosure illustrating the pouch of the specimen retrieval device in a "normal use" configuration and a "release" configuration, respectively.
Figure 17B:
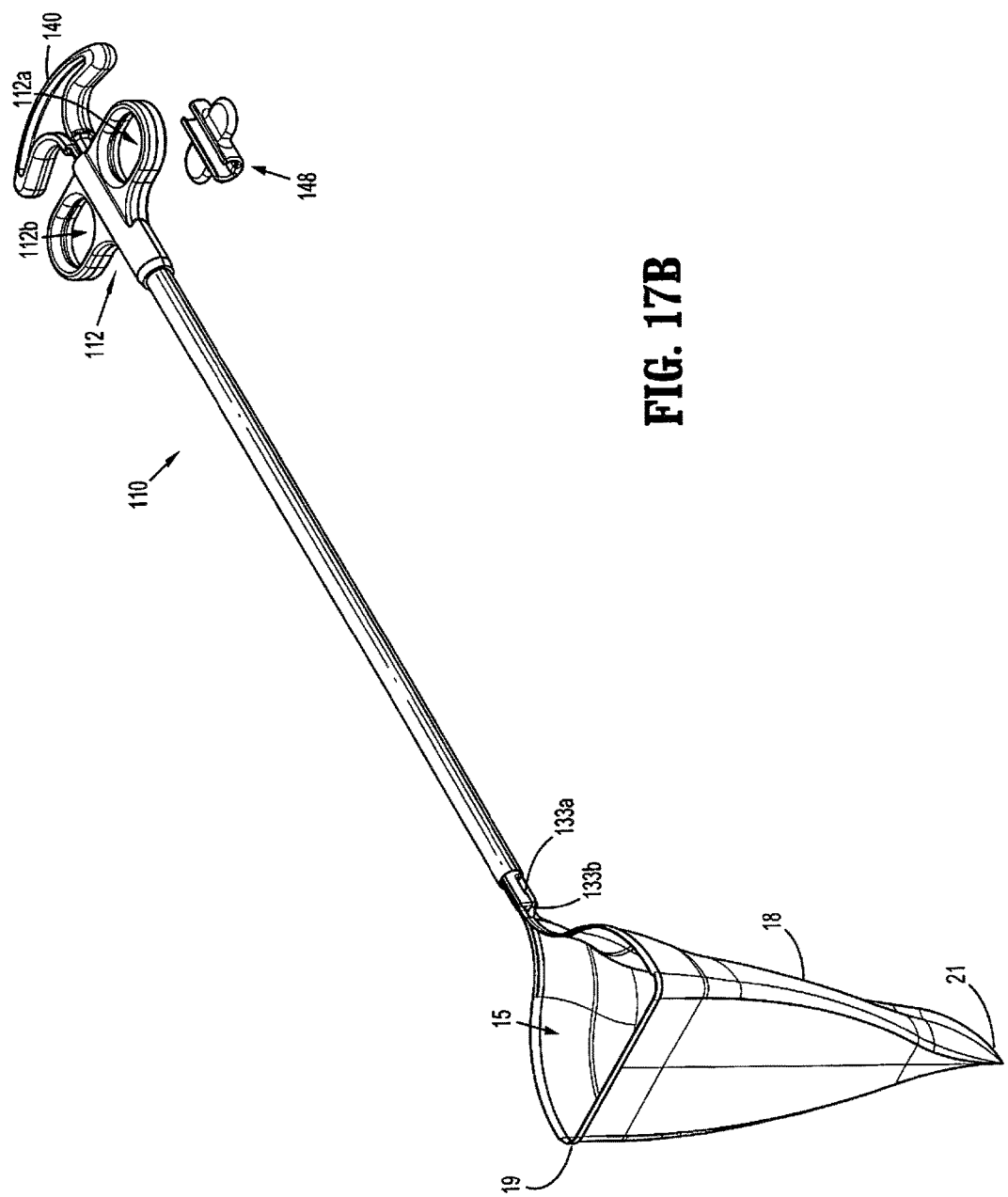
Figure 19:
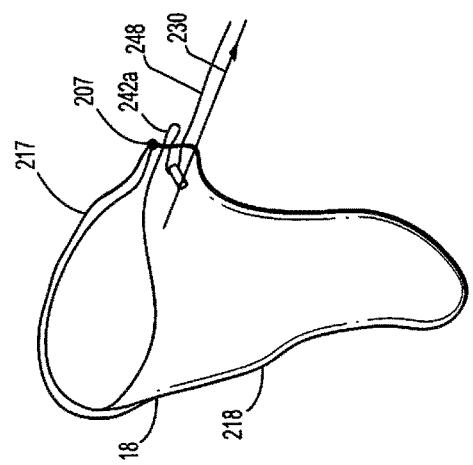
FIG. 19 is a partial, perspective view of a distal end of the specimen retrieval device shown in FIG. 18.

With reference to FIGS. 17A-17B, a specimen retrieval device 110 according to another embodiment of the present disclosure is illustrated. Specimen retrieval device 110 is configured for use with the pouch 18 and is substantially similar to specimen retrieval device 10. Accordingly, only those features that are unique to specimen retrieval device 110 are described in detail herein.

A housing 112 including a pair of optional finger loops 112a, 112b that are configured to receive the fingers of a clinician is provided at a proximal end of the outer shaft 114. Finger loops 112a, 112b are configured to allow the clinician to grasp the housing 112 and move an inner shaft 116 from the extended or "normal use" position (FIG. 17A) to the retracted position.

A cinch handle or puller 148 couples to the inner shaft 116 via a press or friction fit and is positioned between a handle 140 of the inner shaft 116 and finger loops 112a, 112b of housing 112. Cinch puller 148 is configured to contact a proximal end of the housing 112 to limit distal translation of the inner shaft 116 with respect to outer shaft 114 to maintain the distal most end of the retention pin 130 between notch faces 133a, 133b (FIG. 17B). As noted above, with the distal most end of the retention pin 130 positioned between notch faces 133a, 133b, the pouch 18 is attached to the distal end of the inner shaft 116 and is prevented from inadvertently becoming disengaged therefrom. In accordance with the instant disclosure, when a tip 136 of the retention pin 130 engages a flange (not explicitly shown) provided in the outer shaft 114 (see description of distal tip 36 above for example) and inner shaft 116 is moved distally a distance "D," the retention pin 130 is moved proximally relative to the inner shaft 116 such that the distal most end of the retention pin 130 becomes spaced apart from the notch faces 133a, 133b. As a result of this retraction of the retention pin 130, the pouch 18 can be uncoupled from the retention pin 130 in a manner as described above.

The cinch handle 148 may have a suture (not shown) coupled thereto which extends therefrom to couple to the pouch 18 for cinching the pouch 18. The suture may couple to the cinch handle 148 via one or more suitable coupling methods, e.g., adhesive, knot, etc. Moreover, the housing 112 and/or handle 140 may include a cutting mechanism (e.g., the cutting mechanism 51) thereon to cut the suture.

In use, handle assembly 140 may be moved proximally to move inner shaft 116 including pouch 18 to a retracted configuration. Thereafter, outer shaft 114 may be inserted through a natural or man made orifice on a patient and positioned adjacent target tissue. Subsequently, handle assembly 140 may be moved distally to move inner shaft 116 including pouch 18 to a "normal use" configuration, e.g., cinch handle 148 contacts the proximal end of the housing 112.

In the "normal use" configuration, target tissue may be dissected and positioned within pouch 18. A user may selectively and repeatedly move between the normal use and retracted positions so as to collect various different tissue portions at different times during a surgical procedure, while temporarily pulling the entire mouth 15 of the pouch 18 (along with the resilient members 64, 64) into the distal end of the outer shaft 114 between such different times so as to ensure that the contents of the pouch 18 are not spilled between such fillings. When a user is satisfied that all of the tissue to be collected has been placed within pouch 18, a user may remove cinch handle 148 from the inner shaft 116 and move handle assembly 140 distally, e.g., a distance "D." As a result thereof, the tip of the retention pin 130 engages the flange in the housing 112, which, in turn, causes retention pin 130 to move proximally relative to the inner shaft 116, thereby enabling the de-coupling of pouch 18 from the inner shaft 116 in a manner as described above.

The pouch 18 may then be de-coupled from the inner shaft 116, cinched and removed from the patient in a manner as described above. As can be appreciated, the specimen retrieval device 110 overcomes the aforementioned drawbacks typically associated with conventional specimen retrieval devices, e.g., the likelihood of memory wrinkles being formed on pouch 18 is reduced, if not eliminated.

With reference to FIGS. 18-28, a specimen retrieval device 210 according to still another embodiment of the present disclosure is illustrated. Specimen retrieval device 210 is configured for use with the pouch 18 and is substantially similar to the previously described specimen retrieval devices. Accordingly, only those features that are unique to specimen retrieval device 210 are described in detail herein.

Specimen retrieval device 210 includes an outer shaft 214 that is configured to house an inner shaft 216 and a retention pin 230 therein. Unlike the previously described outer shafts, however, outer shaft 214 does not include one of the aforementioned housings. One of the aforementioned housings may, however, be utilized. Moreover, the proximal coupling portion 35 that is configured to mechanically interface with the distal most end of the retention pin 30 may be omitted.

Figure 18:
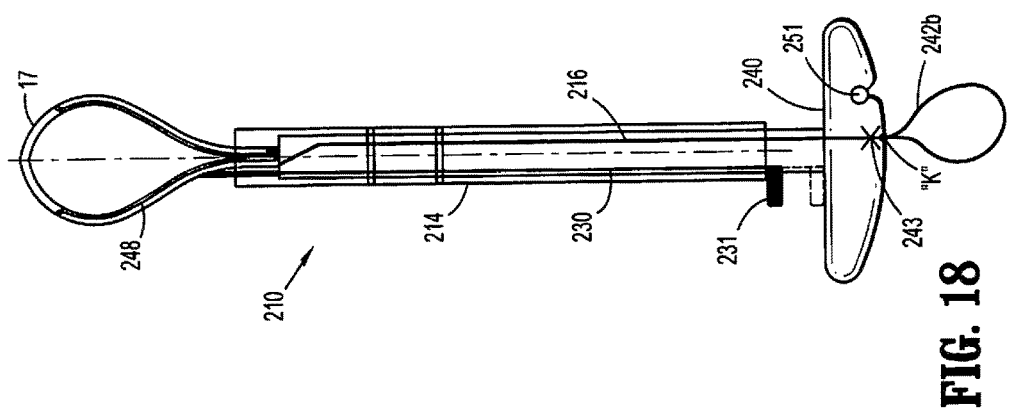
FIG. 18 is a top, elevational view of a specimen retrieval device in accordance with yet another embodiment of the present disclosure.
Figure 20:
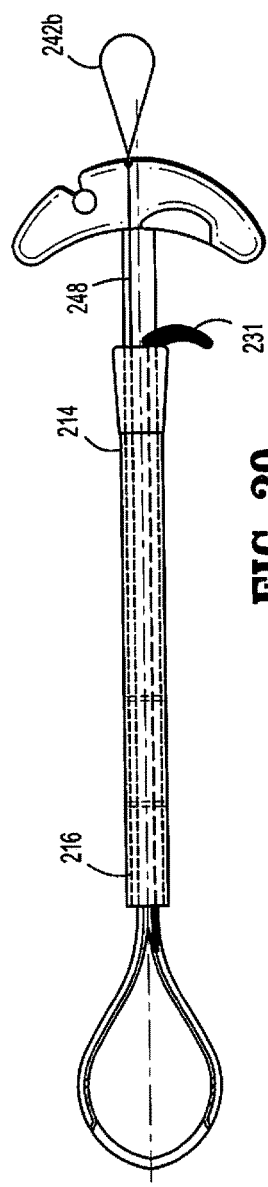
FIG. 20 is a top view of the specimen retrieval device shown in FIG. 18 with a handle assembly and pouch of the specimen retrieval device shown in a shipped position.
Figure 21:
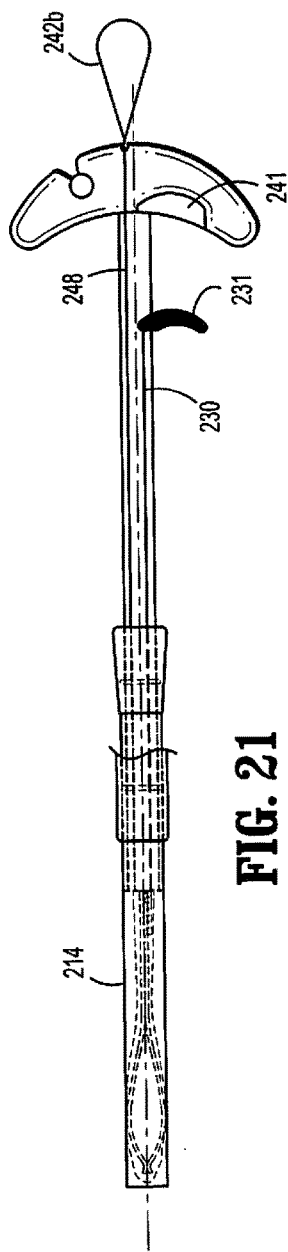
FIG. 21 is a top view of the specimen retrieval device shown in FIG. 18 with the handle assembly and pouch of the specimen retrieval device shown in a retracted position.
Figure 22:
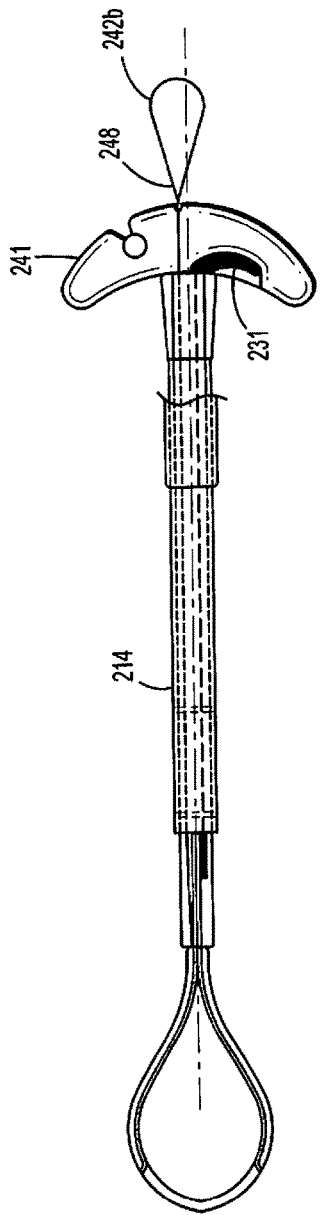
FIG. 22 is a top view of the specimen retrieval device shown in FIG. 18 with the handle assembly and pouch of the specimen retrieval device shown in an extended position.
Figure 23:
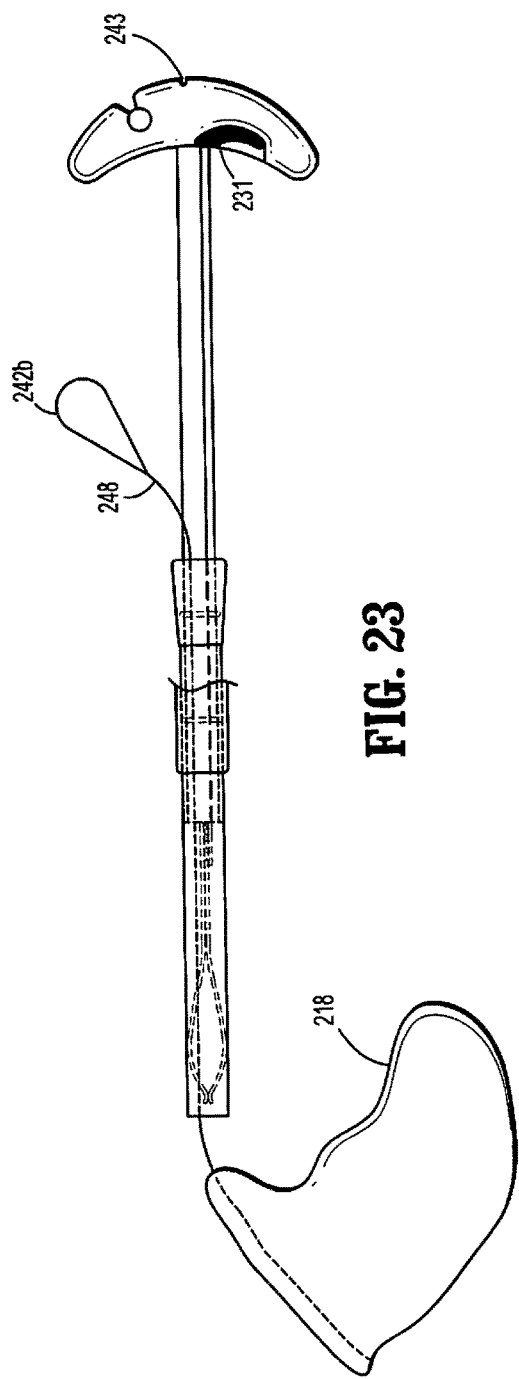
FIG. 23 is a side view of the specimen retrieval device shown in FIG. 18 with the handle assembly shown in the retracted position and with a cinch uncoupled from the handle assembly for cinching the pouch.
Figure 24:
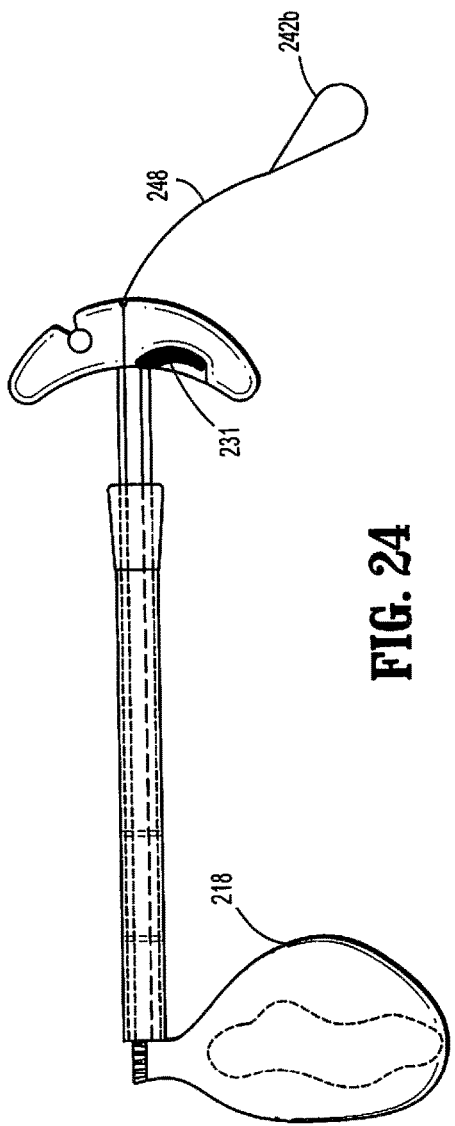
FIG. 24 is a side view of the specimen retrieval device shown in FIG. 18 with the handle assembly shown in the retracted position and with the pouch in a cinched configuration and the cinch disposed in a cutting mechanism of the handle assembly.

The retention pin 230 is coupled to the inner shaft 216 and is moveable within the outer shaft 214 as the inner shaft 216 is moved between the retracted position (FIGS. 21 and 23-24) and extended position (FIGS. 18, 20 and 22). A proximal end 231 of the retention pin 230 is configured to contact a proximal end of the outer shaft 214 (FIGS. 18, 20 and 22). Proximal end 231 includes a generally arcuate configuration and is configured to be received within a corresponding recess 241 (FIG. 21) provided on handle assembly 240 of the inner shaft 216 when the handle assembly 240 is moved to the extended configuration (FIGS. 22-24). A distal most end of the retention pin 230 is configured to releasably couple the retention pin 230 to a proximal portion 235 of a pouch 218, as will be described in greater detail below.

A cinch 248 releasably couples to the handle assembly 240 of the inner shaft and extends through the outer shaft 214 for coupling to the pouch 218. Specifically, a distal end of the cinch 248 fixedly couples to one end of the pouch 218 via an anchor nut 7 (or other suitable device) and extends through the sleeve 17 (see FIG. 19) around a periphery of the pouch 218 and out the other end of the pouch 218. Prior to extending the cinch 248 through the outer shaft 214, the cinch 248 is wrapped around the distal most end of the retention pin 230 to form a first loop 242a (FIG. 19) that is tightened around the distal most end of the retention pin 230 and the proximal end of the pouch 218 to releasably secure the retention pin 230 to the pouch 218. Various loop configurations may be utilized to releasably secure the retention pin 230 to the pouch 218. A proximal end of the cinch 248 includes a second loop 242b (FIG. 18) that is configured to facilitate pulling the cinch 248 for cinching the pouch 218. A knot "K" may be provided adjacent the second loop 242b and may be configured to releasably couple to a corresponding slit 243 disposed at a proximal end of the handle assembly 240. The knot "K" may be utilized to releasably secure the second loop 242b of the cinch to the proximal end of the handle assembly 240.

In use, handle assembly 240 may be moved proximally to move inner shaft 216 including pouch 218 to a retracted configuration (FIG. 21). Thereafter, outer shaft 214 may be inserted through a natural or man made orifice on a patient and positioned adjacent target tissue. Subsequently, handle assembly 240 may be moved distally to move inner shaft 216 including pouch 218 to a "normal use" configuration, e.g., the proximal end 231 of the retention pin 230 contacts proximal end of the outer shaft 214 (FIG. 20).

In the "normal use" configuration, target tissue may be dissected and positioned within pouch 218. A user may selectively and repeatedly move between the normal use and retracted positions in a manner as described above. To uncouple the pouch 218 from the distal end of the retention pin 230, handle assembly 240 is moved distally into contact with the proximal end 231 of the retention pin 230, which, in turn, causes the first loop 242a to move out of engagement with (or uncouple from) the distal most end of the retention pin 230, thereby enabling the de-coupling of pouch 218 from the inner shaft 216 in a manner as described above (FIG. 22).

When a user is satisfied that all of the tissue to be collected has been placed within pouch 218, a user may remove the cinch 248 from the handle assembly 240 of the inner shaft 216 (FIG. 23). The pouch 218 may then be cinched and removed from the patient in a manner as described above (FIG. 24). As can be appreciated, the specimen retrieval device 210 overcomes the aforementioned drawbacks typically associated with conventional specimen retrieval devices, e.g., the likelihood of memory wrinkles being formed on pouch 218 is reduced, if not eliminated.

Figure 25:
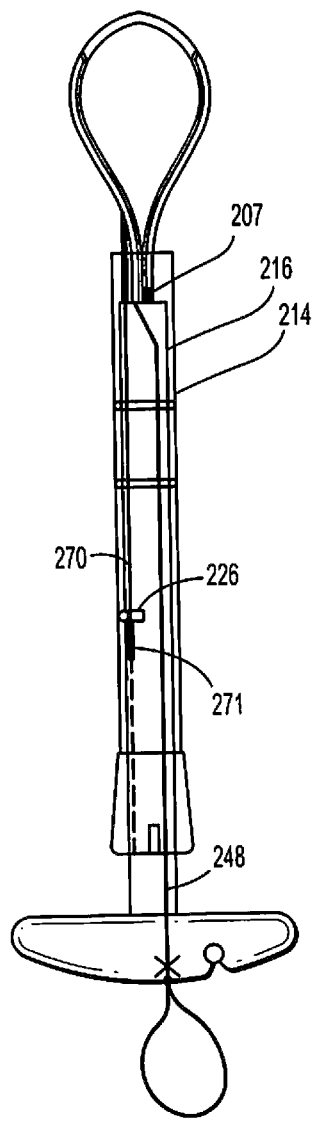
FIG. 25 is a top, elevational view of an alternate embodiment of the specimen retrieval device shown in FIG. 18.

FIG. 25 illustrates an alternate retention pin and outer shaft configuration that may be utilized with the specimen retrieval device 210. Specifically, a retention pin 270 may be provided within the outer shaft 214 and a proximal end 271 of the retention pin 270 may be configured to engage an internal stop, e.g., an internal flange 226, that is defined along an interior wall of the outer shaft 214. In use, a user may selectively and repeatedly move between the normal use and retracted positions in a manner as described above. To uncouple the pouch 218 from the distal most end of the retention pin 270, handle assembly 240 is moved proximally until the proximal end 271 of the retention pin 270 engages the flange 226, which, in turn, causes the first loop 242a to move out of engagement with the distal most end of the retention pin 270, thereby enabling the de-coupling of pouch 218 from the inner shaft 216 in a manner as described above. One or more indicators (not shown) may be provided on the inner shaft 216 and utilized to indicate to a clinician how far the inner shaft 216 has been moved before the inner shaft 216 releases the pouch 218.

Figure 26:
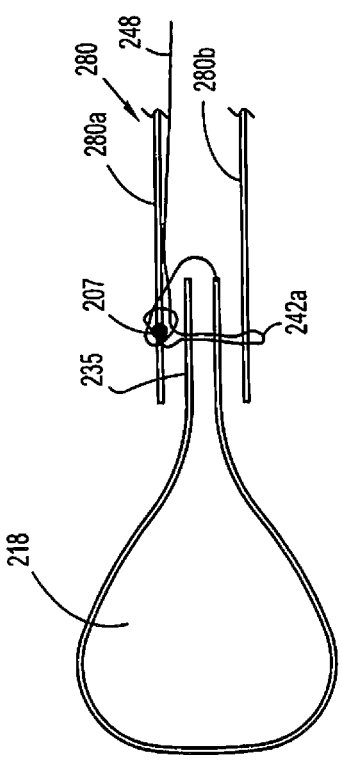
FIG. 26 is a top, elevational view of a distal end of an alternate embodiment of the specimen retrieval device shown in FIG. 18.
Figure 27:
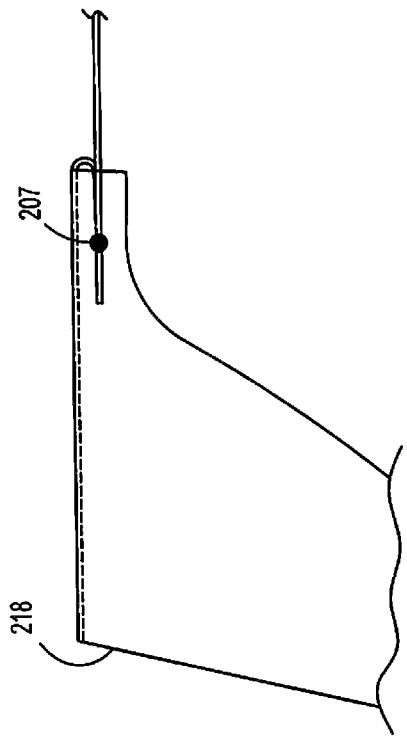
FIG. 27 is a side view of the distal end of the specimen retrieval device shown in FIG. 26.
Figure 28:
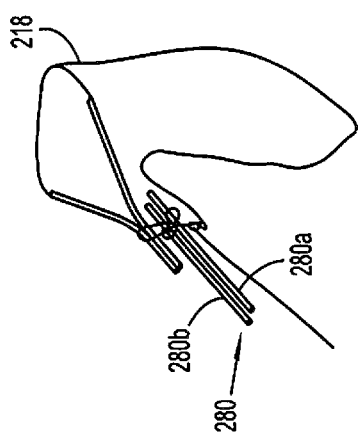
FIG. 28 is a partial, perspective view of the distal end of the specimen retrieval device shown in FIG. 26.

FIGS. 26-28 illustrate an alternate retention pin and outer shaft configuration that may be utilized with the specimen retrieval device 210. Specifically, a retention pin 280 may include a bifurcated configuration having right and left leg members 280a, 280b that are configured to releasably couple to the proximal portion 235 of pouch 218. Specifically, right and left leg members 280a, 280b are configured to squeeze or compress the proximal portion 235 of pouch 218 with a compressive force that, along with the first loop 242a, is capable of maintaining pouch 218 between leg members 280a, 280b as pouch 218 is moved between the retracted and extended configurations.

Leg members 280a, 280b are joined at a proximal end to form a proximal end (not explicitly shown), such as, for example, a proximal end similar to proximal end 231 and/or proximal end 271 that is configured to engage flange 226 and/or proximal end of outer shaft 214. To uncouple the pouch 218 from the distal end of the retention pin 280, handle assembly 240 is moved proximally until the proximal end of the retention pin 280 engages the flange 226 and/or the proximal end of the outer shaft 214, which, in turn, causes the first loop 242a to move out of engagement with the distal most end of the retention pin 280, thereby enabling the de-coupling of pouch 218 from the inner shaft 216 in a manner as described above.

With reference to FIGS. 29A-29C, a specimen retrieval device 310 according to another embodiment of the present disclosure is illustrated. Specimen retrieval device 310 is configured for use with either of the pouches 18 or 218 and is substantially similar to aforementioned specimen retrieval bags. Accordingly, only those features that are unique to specimen retrieval device 310 are described in detail herein.

In accordance with the instant disclosure, specimen retrieval device 310 includes a cinch handle 348 that is in accessible to a clinician when an inner shaft 316 is in the extended position (FIG. 29A). As can be appreciated, this may prevent the clinician from mistakenly cinching the pouch 18 prior to retracting the spring 62, which may lead to the specimen retrieval device not functioning in a manner as intended. To this end, cinch handle 348 includes a generally elongated configuration having a pair of proximal and distal tabs 349a, 349b. A protuberance 346 is provided on an underside of the cinch handle 348 and is configured to facilitate uncoupling the cinch handle 348 from the inner shaft, as will be described below. A suture "S" may be coupled to the cinch handle 348, e.g., a knot "K and aperture configuration, adhesive, etc. Suture "S" may extend along a top surface 345 of the cinch handle 348 and through the housing 312 and outer shaft 314 to couple to the pouch 18.

Housing 312 includes a pair of arm portions 313a, 313b that serve as a handle for a user to grasp. An outer shaft 314 couples to the housing 312 and extends distally therefrom. Housing 312 and outer shaft 314 are configured to allow a user to move the inner shaft 316 from the retracted configuration (FIGS. 29A and 29B) to the extended configuration.

The inner shaft 316 of the specimen retrieval device 310 includes a pocket 317 that is disposed at a proximal end of the inner shaft 316 adjacent a handle assembly in the form of a finger loop 318 that is configured to receive a finger of a clinician. As can be appreciated, finger loop 318 can be replaced with one of the aforementioned a handle assemblies.

Pocket 317 includes a pair of proximal and distal cut-outs 319a, 319b that are configured to releasably engage the pair of proximal and distal tabs 349a, 349b that are provided on the cinch handle 348. A recess or detent 320 (FIG. 29C) is defined within the pocket 317 and is configured to receive the protuberance 346 (FIG. 29B-1) that is provided on an underside of the cinch handle 348.

Depending on which pouch is utilized, the specimen retrieval device 310 may include one more of the aforementioned retention pin configurations (not explicitly shown in FIGS. 29A-29C) to uncouple the pouches 18, 218 from resilient members 64, 66.

In the normal use configuration, the cinch handle 348 will be seated within the pocket 317 and the tabs 349a, 349b of the cinch handle 34 engaged with the cut-outs 319a, 319b (FIG. 29A). In this configuration, the top surface 345 of the cinch handle 348 will be flush with an exterior of the inner shaft 316 to allow a user to repeatedly move the pouch 18 (or pouch 218) in and out of the outer shaft 314.

A user can uncouple the pouch 18 (or pouch 218) from the resilient members 64, 66 in accordance with one of the aforementioned embodiments described above. Thereafter the user can cinch the pouch 18 (or pouch 218). Specifically, a user can move the tab 349a out of engagement with the cut-out 319a, which, in turn, simultaneously causes the protuberance 346 to rotate within the recess 320 and the tab 349b of the cinch handle 348 to pivot about the cut-out 319b of the inner shaft 316 (FIG. 29B). A user can then remove the cinch handle 348 from the pocket 317 of the inner shaft 316 and pull the cinch handle 348 proximally to cinch the pouch 18 (FIG. 29C).

Figures 30A, 30B, 30C, 31, 32:
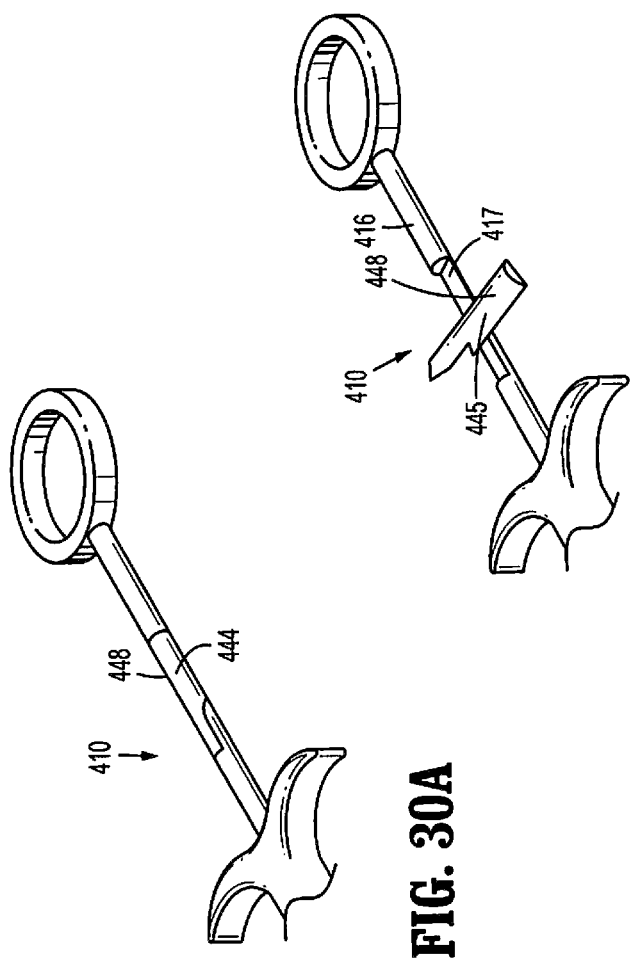
FIGS. 30A-30C are partial, perspective views of a specimen retrieval device in accordance with still yet another embodiment of the present disclosure with a cinch handle of the specimen retrieval device shown in various positions.
FIG. 31 is a perspective view of an alternate embodiment of a cinch handle configured for use with the specimen retrieval devices shown in FIGS. 29A-29C and 30A-30C.
FIG. 32 is an end view taken along section line 32-32 in FIG. 31.

With reference to FIGS. 30A-30C, a specimen retrieval device 410 according to another embodiment of the present disclosure is illustrated. Specimen retrieval device 410 is configured for use with either the pouch 18 or pouch 218 and is substantially similar to aforementioned specimen retrieval bags, e.g., specimen retrieval device 310. Accordingly, only those features that are unique to specimen retrieval device 410 are described in detail herein.

A pocket 417 is provided on an inner shaft 416 and includes a protrusion 421 that releasably couples via a press or friction fit to an aperture or indent 444 (FIG. 30C) provided on a cinch handle 448. The suture "S" may be coupled to the cinch handle 448 via one of the aforementioned coupling methods. Moreover, one or more optional cut outs and/or tab members (see discussion above for example) may be utilized to facilitate coupling the cinch handle 448 within the pocket 417.

In the normal use configuration, the cinch handle 448 will be seated within the pocket 417 (FIG. 30A). In this configuration, a top surface 445 of the cinch handle 448 will be flush with an exterior of the inner shaft 416 to allow a user to repeatedly move the pouch 18 (or pouch 218) in and out of the outer shaft 414.

A user can uncouple the pouch 18 (or pouch 218) from the resilient members 64, 66 in a manner as described above. Thereafter the user can cinch the pouch 18 (or pouch 218). Specifically, a user can rotate the cinch handle 448 about the protuberance 346 to place the cinch handle 448 in a position for allowing a clinician to uncouple the cinch handle 448 from the pocket 417 of the inner shaft 416 (FIG. 30B). A user can then remove the cinch handle 448 from the pocket 417 of the inner shaft 416 and pull the cinch handle 448 proximally to cinch the pouch 18 (or pouch 218), FIG. 30C.

In accordance with the instant disclosure, other cinch handles may utilized with the specimen retrieval devices 310, 410. For example, FIGS. 31-32 illustrate a cinch handle 548 that includes two generally arcuate lateral portions 549*a*, 549*b* and an elongated medial portion 547 that extend at least partially along a length of the cinch handle 548. The medial portion 547 is configured to seat within a corresponding indent or groove (not explicitly shown) that may be defined within the pockets 317, 417. The lateral portions 549*a*, 549*b* are relatively flexible and configured to snap into place along an exterior of the inner shafts 316, 416. Accordingly, the lateral portions 549*a*, 549*b* should extend beyond a center of the inner shafts 316, 416 (see FIG. 32 for example). A user can uncouple the cinch handle 548 from the pockets 317, 417 of the inner shafts 316, 416, respectively, via grasping (or squeezing) the lateral portions 549*a*, 549*b* of the cinch handle 548 while simultaneously rotating (or pulling) the cinch handle 548 until the cinch handle 548 uncouples from the pockets 317, 417 of the respective inner shafts 316, 416.

Figure 34:
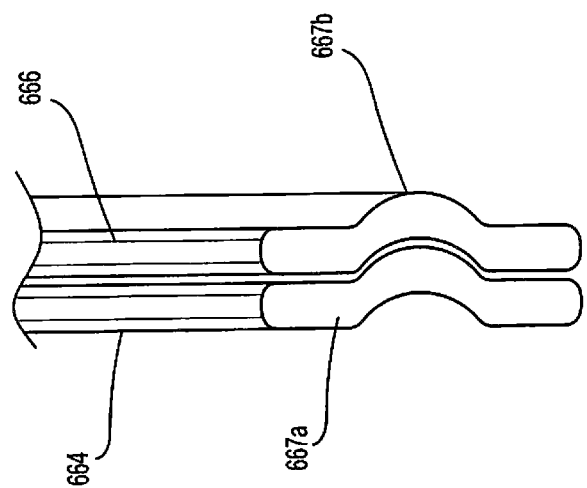
FIG. 34 is a front view of the resilient member shown in FIG. 33 with a distal end thereof shown in a nested configuration.
Figure 33:
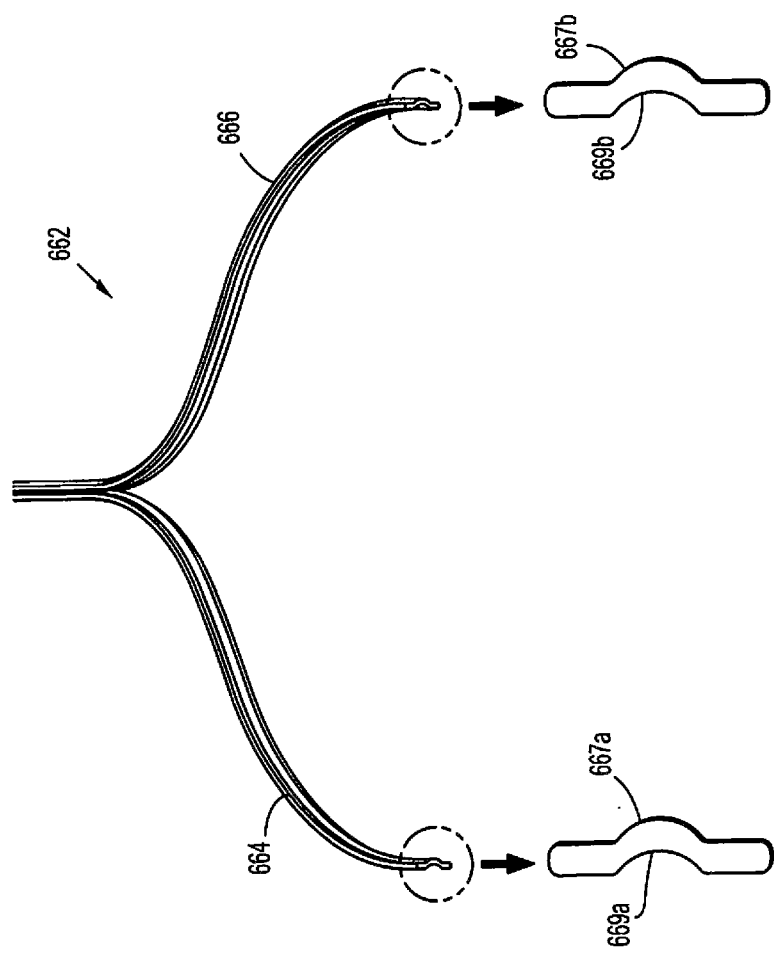
FIG. 33 is a front view of a resilient member configured for use with any of the aforementioned specimen retrieval devices.

With reference to FIGS. 33-34, an alternate embodiment of the spring 62 is illustrated and is designated spring 662. Spring 662 is similar to spring 62 and configured for use with any of the aforementioned specimen retrieval devices and pouches. Accordingly, only those features that are unique to spring 662 are described in detail herein.

Spring 662 includes two resilient fork members 664, 666 having respective distal tips 667*a*, 667*b* with generally arcuate medial portions 669*a*, 669*b* that form a nested configuration when the resilient fork members 664, 666 are in a compressed configuration, see FIG. 34 for example.

In embodiments, such as the illustrated embodiment, the distal tips 667*a*, 667*b* are monolithically formed with resilient fork members 664, 666. Alternatively, distal tips 667*a*, 667*b* may be formed as separate components and, subsequently, coupled to resilient fork members 664, 666 via one or more suitable coupling methods, e.g., adhesive, mechanical interface, or the like.

The complementary geometry distal tips 667*a*, 667*b* allows the resilient fork members 664, 666 to nest on each other, as opposed to overlapping or moving over one another (commonly referred to in the art as "fork scissoring") as with conventional springs. This fork scissoring may damage the sleeve 17 of the pouches 18, 218 and/or may increase the likelihood of uncontrolled bunching of the pouch 18, 218 as the pouch 18, 218 is moved between the extended and retracted positions. In accordance with the instant disclosure, the nesting of the resilient fork members 664, 666 may help to reduce withdrawal force associated with the pouch 18, 218 and may help to promote better withdrawal into the previously described outer shafts of specimen retrieval devices.

In use, when the pouch 18 is positioned within one of the aforementioned shafts, e.g., outer shaft 114, and being moved therein, resilient fork members 664, 666 are guided to the nested configuration as a result of the complementary geometry distal tips 667*a*, 667*b*.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A specimen retrieval device, comprising:
    an outer shaft defining a bore therethrough;
    an inner shaft slidingly disposed within the bore of the outer shaft, the inner shaft having a handle and a pouch retention mechanism including one or more protrusions and at least one member;
    a pouch connected to the inner shaft by the pouch retention mechanism, the pouch including one or more openings positioned to receive the one or more protrusions; and
    an actuator for actuating the pouch retention mechanism so as to permit a user to selectively detach the pouch from the inner shaft, the actuator being movably connected to the handle, the at least one member being movable, in response to movement of the actuator, from a first position preventing separation of the pouch from the one or more protrusions to a second position facilitating separation of the pouch from the one or more protrusions, wherein the at least one member moves longitudinally along an outer surface of the inner shaft.

2. The specimen retrieval device according to claim 1, wherein the actuator is a ring.

3. The specimen retrieval device according to claim 2, wherein the ring is pivotably connected to the handle.

4. The specimen retrieval device according to claim 3, wherein the handle defines a void, the ring having a portion that extends radially into the void so as to provide a surface for a user's finger to pivot the ring relative to the handle.

5. The specimen retrieval device according to claim 1, wherein the at least one member moves by sliding relative to the inner shaft.

6. The specimen retrieval device according to claim 1, wherein the pouch includes two openings through which the pouch retention mechanism extends.

7. A specimen retrieval device, comprising:
    an outer shaft defining a bore therethrough;
    an inner shaft slidingly disposed within the bore of the outer shaft, the inner shaft having a handle and a pouch retention mechanism including one or more protrusions and at least one member;
    a pouch connected to the inner shaft by the pouch retention mechanism, the pouch including one or more openings positioned to receive the one or more protrusions;
    an actuator for actuating the pouch retention mechanism so as to permit a user to selectively detach the pouch from the inner shaft, the actuator being movably connected to the handle, the at least one member being movable, in response to movement of the actuator, from a first position preventing separation of the pouch from the one or more protrusions to a second position facilitating separation of the pouch from the one or more protrusions; and a cinch having a proximal end, the proximal end of the cinch being connected to the actuator, the actuator being configured, when actuated, to pull the cinch a first distance so as to move the pouch retention mechanism proximally relative to the inner shaft.

8. The specimen retrieval device according to claim 7, wherein the cinch is one of a suture, a thread, a wire or a cable.

9. The specimen retrieval device according to claim 8, further comprising a pouch support mechanism connected to the inner shaft and configured to support the pouch.

10. The specimen retrieval device according to claim 9, wherein the pouch support mechanism includes a pair of resilient forks.

11. The specimen retrieval device according to claim 10, wherein the pouch includes a slot around the circumference of the mouth of the pouch, and the pair of forks of the pouch support mechanism are configured to reside within the slots when the pouch is connected to the inner shaft and to be withdrawn out of the slots when the pouch is disconnected from the inner shaft.

12. The specimen retrieval device according to claim 11, wherein the cinch also resides in the slot around the circumference of the mouth of the pouch.

13. The specimen retrieval device according to claim 12, wherein the cinch is further configured, when pulled proximally a second distance, to cause the mouth of the pouch to close.

14. A specimen retrieval device, comprising:
an outer shaft defining a bore therethrough;
an inner shaft slidingly disposed within the bore of the outer shaft, the inner shaft having a distal end, a handle and a pouch retention mechanism including at least one member and one or more protrusions near the distal end of the inner shaft;
a pouch connected to the inner shaft by the pouch retention mechanism; and
an actuator for actuating the pouch retention mechanism so as to permit a user to selectively detach the pouch from the inner shaft, the actuator being movably connected to the handle;
wherein the at least one member moves longitudinally along an outer surface of the inner shaft and abuts the one or more protrusions such that the pouch remains attached to the one or more protrusions when the at least one member is in a distal position relative to the inner shaft.

15. The specimen retrieval device according to claim 14, wherein, when the at least one member is moved proximally relative to the inner shaft by actuation of the actuator, a distal end of the at least one member is retracted such that the at least one member no longer abuts the one or more protrusions, thereby allowing the one or more protrusions to slide out of engagement with the opening of the pouch and the pouch to be disconnected from the pouch retention mechanism.

* * * * *